United States Patent
Fredriksson et al.

(10) Patent No.: US 12,252,738 B2
(45) Date of Patent: Mar. 18, 2025

(54) ROLLING CIRCLE AMPLIFICATION PRODUCT HAVING MULTIPLE FREE ENDS

(71) Applicant: PIXELGEN TECHNOLOGIES AB, Solna (SE)

(72) Inventors: Simon Fredriksson, Bromma (SE); Filip Karlsson, Solna (SE)

(73) Assignee: PIXELGEN TECHNOLOGIES AB, Stockholm (SE)

( * ) Notice: Subject to any disclaimer, the term of this patent is extended or adjusted under 35 U.S.C. 154(b) by 0 days.

(21) Appl. No.: 18/276,231

(22) PCT Filed: Mar. 29, 2022

(86) PCT No.: PCT/IB2022/052861
§ 371 (c)(1),
(2) Date: Aug. 7, 2023

(87) PCT Pub. No.: WO2022/208326
PCT Pub. Date: Oct. 6, 2022

(65) Prior Publication Data
US 2024/0301471 A1 Sep. 12, 2024

Related U.S. Application Data

(60) Provisional application No. 63/168,127, filed on Mar. 30, 2021.

(51) Int. Cl.
*C12Q 1/6813* (2018.01)
*C12Q 1/6844* (2018.01)

(52) U.S. Cl.
CPC ......... *C12Q 1/6813* (2013.01); *C12Q 1/6844* (2013.01)

(58) Field of Classification Search
CPC ............... C12Q 1/6806; C12Q 1/6813; C12Q 2525/301
See application file for complete search history.

(56) References Cited

U.S. PATENT DOCUMENTS 11,155,858 B2 * 10/2021 Glezer ................ C12Q 1/6853
2021/0198730 A1 * 7/2021 Glezer ................ C12Q 1/6853

FOREIGN PATENT DOCUMENTS

WO    WO 2006/108423 A2    10/2006
WO    WO 2006/108423 A3    10/2006
(Continued)

OTHER PUBLICATIONS

Lizardi et al., "Mutation detection and single-molecule counting using isothermal rolling-circle amplification", Nature Genetics, 1998, 19(3): 225-232.
(Continued)

*Primary Examiner* — Young J Kim
(74) *Attorney, Agent, or Firm* — James S. Keddie; Bozicevic, Field & Francis LLP

(57) ABSTRACT

Described herein is a complex comprising multiple nucleic acid molecules that are hybridized together, each comprising, from 5' to 3', a first complementary sequence, a spacer sequence and a second complementary sequence, and either/or a 5' end sequence that is 5' of the first complementary sequence and terminates in a 5' phosphate and a 3' end sequence that is 3' of the second complementary sequence and terminates in a 3' hydroxyl. In this complex: the first complementary sequence of one molecule is directly or indirectly hybridized with the second complementary sequence of another molecule in the complex and the spacer sequence and the 3' and/or 5' end sequences are single-stranded. Methods of making and using the complex are also provided.

18 Claims, 15 Drawing Sheets

Specification includes a Sequence Listing.

(56) References Cited

FOREIGN PATENT DOCUMENTS

WO    WO 2014/076214 A1    5/2014
WO    WO 2015/079042 A1    6/2015

OTHER PUBLICATIONS

Wu et al., "Profiling surface proteins on individual exosomes using a proximity barcoding assay", Nature Communications, Aug. 2019, 10(1): 3854, 10 pages.

* cited by examiner

Step 1, for RCP with hairpins containing a nicking restriction site

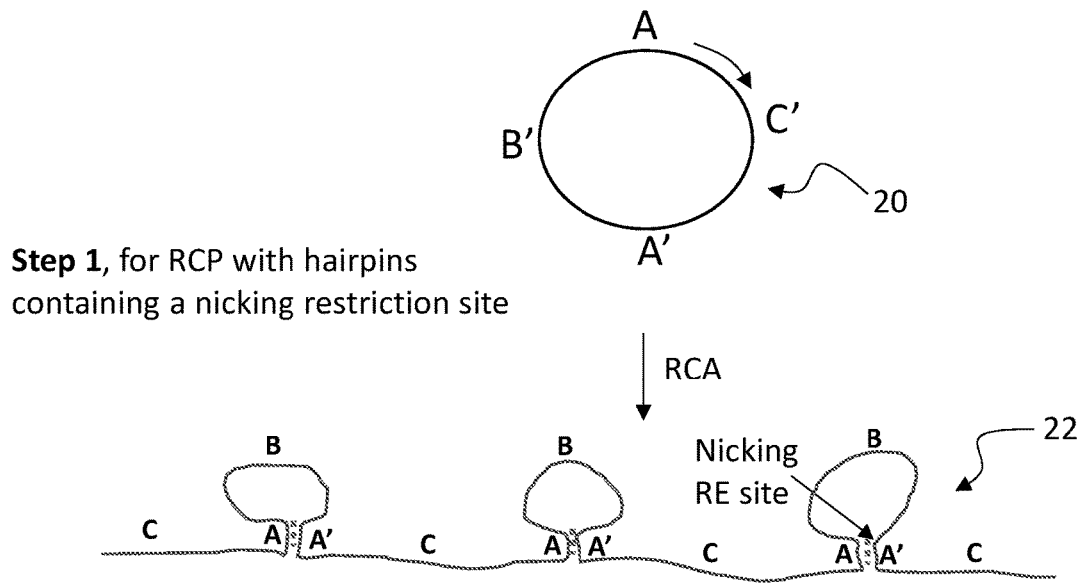

Step 2, Nick the RE-site to liberate either a free 3' end or a free 5'phosphate end. This still maintains the Pixels integrity by having a sufficiently stable former hairpin, now dsDNA.

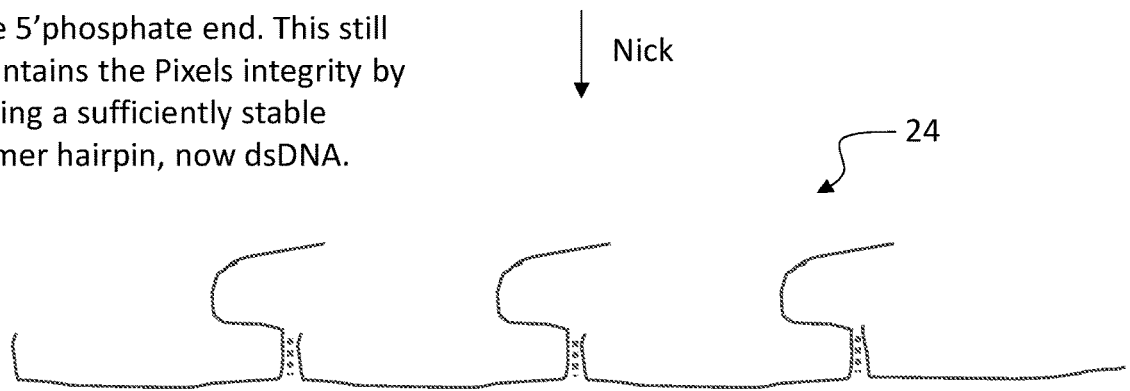

The resulting RCP-Pixel will be a cluster of copies of a UMI with free ends held together by the hairpin. The pixel is capable of interacting with probes to from a pixel mesh image.

FIG. 2

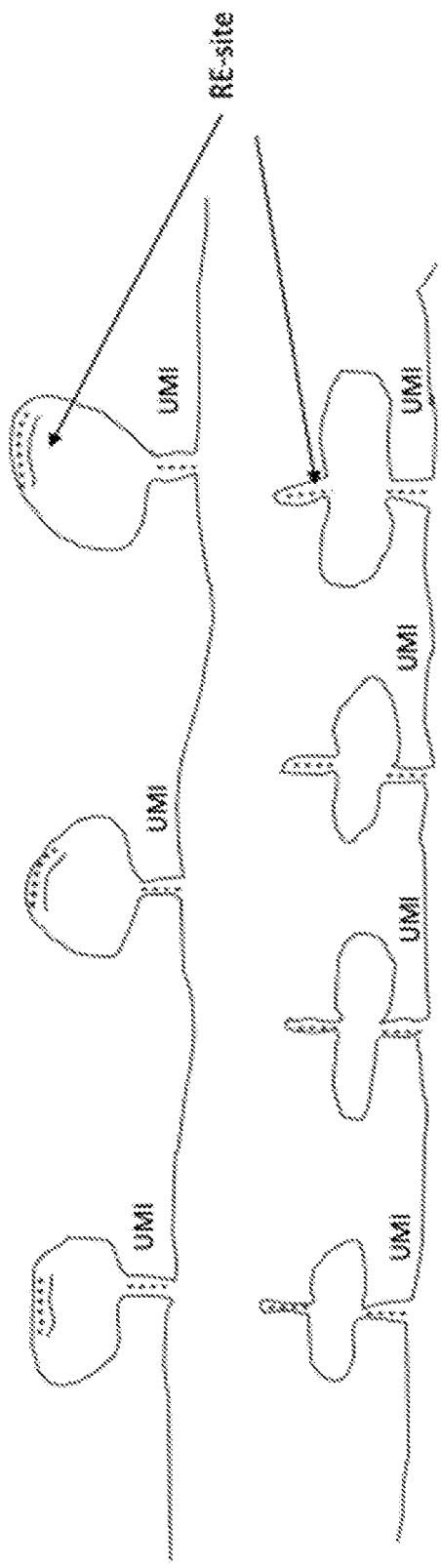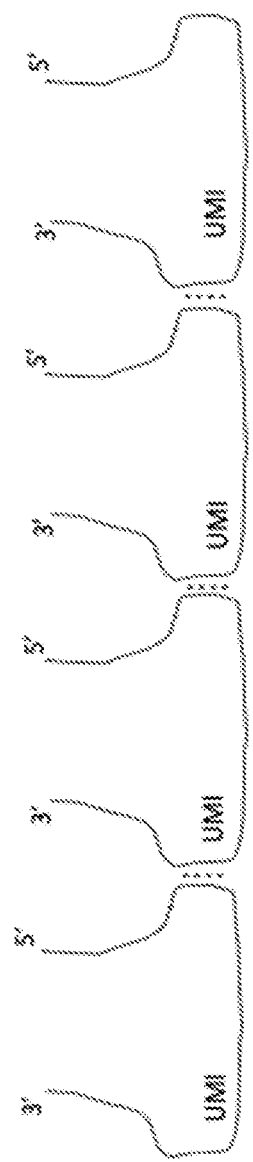
FIG. 3

ROLLING CIRCLE AMPLIFICATION PRODUCT HAVING MULTIPLE FREE ENDS

CROSS-REFERENCING

This application is a § 371 national phase of International Application No. PCT/IB2022/052861, filed on Mar. 29, 2022, which claims the benefit of U.S. provisional application Ser. No. 63/168,127, filed on Mar. 30, 2021, which applications are incorporated by reference herein in their entireties.

BACKGROUND

Rolling circle amplification (RCA) products typically contain hundreds or thousands of tandem repeats of the same sequence, copied from a circular molecule. The use of RCA products is limited, however, because each molecule only contains one 3' end and one 5' end. For example, while one can potentially hybridize labeled oligonucleotides with a repeat in an RCA product, there is little or no opportunity to ligate or copy sequences from other molecules onto an RCA. This disclosure solves this problem.

SUMMARY

Described herein is a complex comprising multiple nucleic acid molecules that are hybridized together, each comprising, from 5' to 3', a first complementary sequence, a spacer sequence and a second complementary sequence, and either/or a 5' end sequence that is 5' of the first complementary sequence and terminates in a 5' phosphate and a 3' end sequence that is 3' of the second complementary sequence and terminates in a 3' hydroxyl. In this complex: the first complementary sequence of one molecule is directly or indirectly hybridized with the second complementary sequence of another molecule in the complex and the spacer sequence and the 3' and/or 5' end sequences are single-stranded. Methods of making and using the complex are also provided.

In some embodiments, the first and second complementary sequences are complementary to one another, and, in the complex: the first complementary sequence of one molecule is directly hybridized with the second complementary sequence of another molecule in the complex.

In some embodiments, the first and second complementary sequences are complementary to a splint nucleic acid, and, in the complex: the first complementary sequence of one molecule is indirectly hybridized with the second complementary sequence of another molecule in the complex via the splint nucleic acid.

The complex may be used in variety of assays. For example, in some embodiments a complex may be used in a method that comprises hybridizing a complex with a target polynucleotide, wherein the 3' or 5' end sequence of a nucleic acid molecule of the complex hybridizes with the target polynucleotide to produce a duplex; extending the nucleic acid molecule or the target polynucleotide (by ligation or a polymerase) using the other member of the duplex as a template to produce an extension product; and sequencing the extension product.

In some embodiments, the complex may be made by a method comprising: (a) amplifying a circle of nucleic acid by rolling circle amplification (RCA) to make an RCA product, wherein the circle comprises: (i) a first complementary sequence that, in double stranded form, contains a recognition sequence for a nicking endonuclease; (ii) a spacer sequence; (iii) a second complementary sequence that is complementary to the first complementary sequence; and (iv) an end sequence; wherein the RCA product comprises multiple tandem repeats of sequences (i)-(iv), and, in each repeat the first complementary sequence and the first complementary sequence hybridize together to form double-stranded region that contains the recognition sequence for the nicking endonuclease, and the end sequence forms a loop; and (b) digesting the product of step (a) with the nicking endonuclease, to nick the double-stranded region close to the loop and release a free end that comprises the end sequence.

In some embodiments, the complex may be made by a method comprising (a) amplifying a circle of nucleic acid by rolling circle amplification (RCA) to make an RCA product, wherein the circle comprises complements of: (i) a first complementary sequence that, in double stranded form, contains a recognition sequence for a nicking endonuclease or restriction endonuclease; (ii) a spacer sequence; (iii) a second complementary sequence; and (iv) an end sequence; wherein the RCA product comprises multiple tandem repeats of sequences (i)-(iv), and (b) hybridizing the RCA product to a splint nucleic acid that hybridizes to sequences (i) and (iii) but not sequences (ii) and (iv) in the RCA product, to produce loops and a double-stranded region that contains a recognition sequence for the nicking endonuclease or restriction endonuclease; and (c) digesting the product of step (b) with the nicking endonuclease or restriction endonuclease, to nick the double-stranded region close to the loops and release free ends that comprises the end sequence. In these embodiments, the splint nucleic acid may be an oligonucleotide or another RCA product, for example.

These and other uses may be apparent from the present disclosure.

BRIEF DESCRIPTION OF THE FIGURES

The skilled artisan will understand that the drawings, described below, are for illustration purposes only. The drawings are not intended to limit the scope of the present teachings in any way.

FIG. 2 schematically illustrates a method by which complexes that have free 3' or free 5' ends can be made.

FIG. 3 schematically illustrates method for producing complexes that have free 3' and 5' ends.

DEFINITIONS

Figure 1:
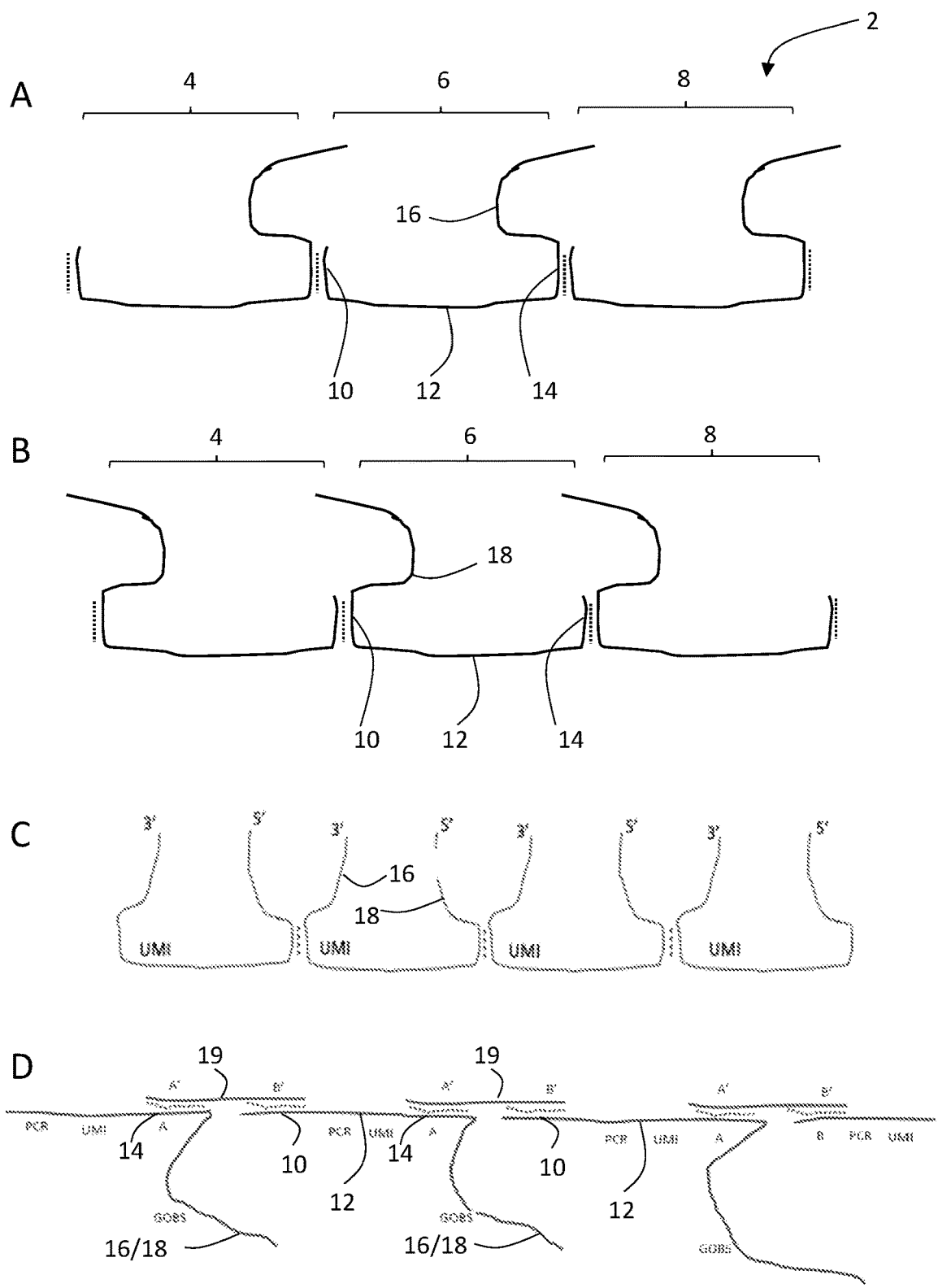
FIG. 1 schematically illustrates complexes having free 3' ends (A), 5' ends (B), and 3' and 5' ends (C). As show, these complexes are held together by base pairing between different nucleic acid molecules.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA, various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes.

LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence or fragment, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by, e.g., Illumina, Life Technologies, BGI Genomics (Complete Genomics technology), and Roche etc. Next-generation sequencing methods may also include nanopore sequencing methods or electronic-detection based methods such as, e.g., Ion Torrent technology commercialized by Life Technologies.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to forms of measurement, and include determining if an element is present or not. These terms include both quantitative and/or qualitative determinations. Assessing may be relative or absolute.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "set" and "population" are used interchangeably to refer to something that contains at least 2 members. In certain cases, a plurality may have at least 10, at least 100, at least 100, at least 10,000, or at least 100,000 members.

A "primer binding site" refers to a site to which an oligonucleotide hybridizes in a target polynucleotide or fragment. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

The term "extending", as used herein, refers to the extension of a nucleic acid by ligation or the addition of nucleotides using a polymerase. If a nucleic acid that is annealed to a polynucleotide is extended, the polynucleotide acts as a template for an extension reaction. In these embodiments, the nucleic acid may be extended by a template-dependent polymerase or by ligation to an oligonucleotide that is complementary to the polynucleotide, where the polynucleotide acts as a splint.

As used herein, the term "rolling circle amplification" or "RCA" for short refers to an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" refers to the concatemerized products of a rolling circle amplification reaction.

As used herein, the term "surface" refers to any solid material (e.g. glass, metal, ceramics, organic polymer surface or gel) that may contain cells or any combinations of biomolecules derived from cells, such as proteins, nucleic acids, lipids, oligo/polysaccharides, biomolecule complexes, cellular organelles, cellular debris or excretions (exosomes, microvesicles), etc. Tissue blots, western blots and glass slides are examples of solid materials that have a surface. Cells, e.g., suspensions of mammalian cells, are another example of a surface.

As used herein, the term "splint" refers to a nucleic acid, e.g., an oligonucleotide, that hybridizes to two other non-contiguous sequences in the same molecule (in which case hybridization will result in a bubble), or sequences in different molecules. In some cases, a splint==brings ends together to produce a ligatable junction.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 10:
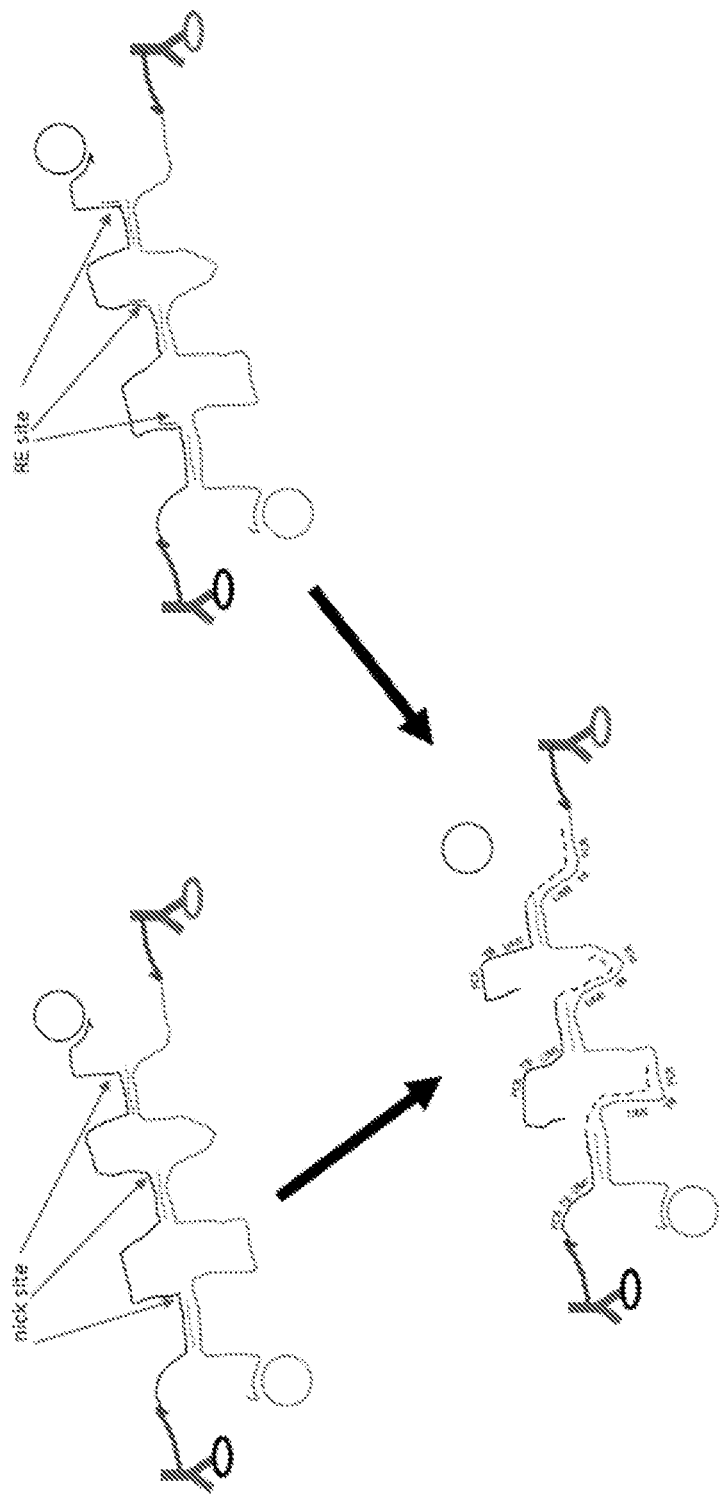
FIG. 10 schematically illustrates an alternate embodiment that uses RCA products produced using the probe system shown in claim 9.

With reference to FIG. 1, in some embodiments, complex 2 may comprise multiple nucleic acid molecules (e.g., 4, 6, 8) that are hybridized together. As shown, each nucleic acid molecule comprises, from 5' to 3': i. a first complementary sequence 10, ii. a spacer sequence 12, and iii. a second complementary sequence 14. As illustrated in panels A-C, the first and second complementary sequence may be complementary to one another. In these embodiments, the complex is held together by hybridization of the first complementary sequence from one molecule with the second complementary sequence of another molecule. In these embodiments, the first and second complementary sequences are "directly" hybridized to one another. As illustrated in panel D, the first and second complementary sequence may be complementary a splint nucleic acid 19 that hybridizes to the end of those sequences, which may be an oligonucleotide (as shown in FIG. 1) or another RCA product (as illustrated in FIG. 10). In these embodiments, the complex is held together by hybridization of the first and second complementary sequences to the splint nucleic acid. As illustrated, the complex can have free 3' ends (panel A), free 5' ends (panel B) or free 3' and 5' ends (panel C). The ends in panel D can be 3' or 5' ends. In the embodiment shown in panel A, each molecule contains a free (i.e., unhybridized) 3' end sequence 16 that is 3' of the second complementary sequence and terminates in a 3' hydroxyl. In this embodiment, the spacer sequence 12 and the 3' end sequence 16 are single-stranded. In the embodiment shown in panel B of FIG. 1, each molecule contains a free (i.e., unhybridized) 5' end sequence 18 sequence that is 5' of the first complementary sequence and terminates in a 5' phosphate. In this embodiment, the spacer sequence 12 and the 5' end sequence 18 are single-stranded. In the embodiment shown in panel C of FIG. 1, each molecule contains a free (i.e., unhybridized) 5' end sequence 18 and a free (i.e., unhybridized) 3' end sequence, where the free 5' end sequence 18 sequence is 5' of the first complementary sequence and terminates in a 5' phosphate and the free 3' end sequence 16 is 3' of the second complementary sequence and terminates in a 3' hydroxyl. The same principles can be applied to panel D of FIG. 1. As such, in addition to the first complementary sequence 10, a spacer sequence 12, and second complementary sequence 14, each molecule may further comprise a 5' end sequence that is 5' of the first complementary sequence and terminates in a 5' phosphate; and/or a 3' end sequence that is 3' of the second complementary sequence and terminates in a 3' hydroxyl. wherein, in the complex: i. the first complementary sequence of one molecule is directly or indirectly hybridized with the second complementary sequence of another molecule in the complex and ii. the spacer sequence and the 3' and/or 5' end sequences are single-stranded.

The illustrated complexes contain 3 or 4 of the nucleic acid molecules. In practice, the complex may comprise at least 10, at least 50, at least 100, at least 500 or at least 1,000 of the nucleic acid molecules, many of which will be held together in a chain by direct or indirect hybridization of the first complementary sequence of one molecule to the second complementary sequence of another. In these embodiments, the first complementary sequence, the spacer sequence, a second complementary sequence, and the 3' and/or 5' end sequences (whichever are in the molecules) may be identical in all of the molecules.

As noted above, in some embodiments, the first and second complementary sequences are complementary to one another. In this complex: i. the first complementary sequence of one molecule is directly hybridized with the second complementary sequence of another molecule in the complex.

In some embodiments, the first and second complementary sequences are complementary to a splint nucleic acid. In the complex: i. the first complementary sequence of one molecule is indirectly hybridized with the second complementary sequence of another molecule in the complex via the splint nucleic acid. In these embodiments, if the splint nucleic acid is a splint oligonucleotide then it may be blocked at the 3' end and/or 5' end (i.e., is modified so that it is not contain a 3' hydroxyl or a 5' phosphate), thereby preventing it from participating in future ligation and/or polymerase-catalyzed extension reactions. In some embodiments, depending on how the complexes are made, a splint oligonucleotide may additionally contain one or more nuclease-resistant linkages, e.g., one or more phosphorothioate linkages, which linkages may protect the oligonucleotide from being cleaved by a restriction endonuclease during manufacture of the complex.

Figure 8:
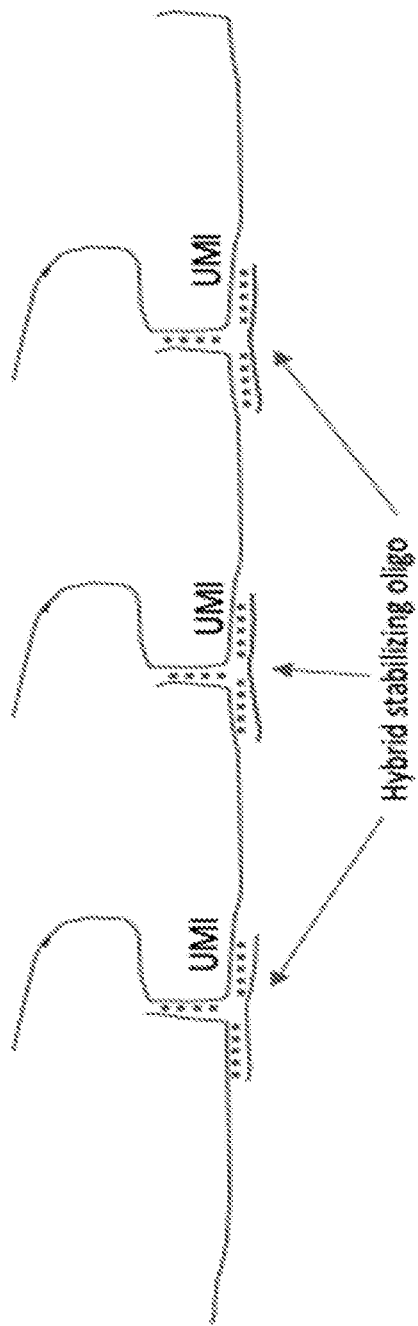
FIG. 8 schematically illustrates how complexes can be stabilized, if desirable.

The lengths of the component parts of a nucleic acid molecule in the complex may vary. In some embodiments, the first and second complementary sequences are at least 8, at least 15, or at least 20 nucleotides in length (e.g., 20-60 or 30-50 nucleotides in length), wherein as the spacer sequence may be at least 5 nucleotides in length (e.g., 10-50 nucleotides) and the 3' and/or 5' end sequences may be at least 5 nucleotides in length (e.g., 10-50 nucleotides). In some embodiments, the first and second complementary sequences may be relatively long, e.g., 30-50 nucleotides in length or may have a higher G/C content, so that the complex stays intact under the conditions used to hybridize the free ends to another molecule. In some embodiments, the molecules could be held together by hybridization of a stabilizing oligonucleotide, as illustrated in FIG. 8. The splint nucleic acid may be oligonucleotide or, as illustrated in FIG. 10, another RCA product. If the splint nucleic acid is a splint oligonucleotide, then the splint oligonucleotide may be 20-100 nucleotides in length and may have a first sequence that is at least 15, at least 20, or at least 30 nucleotides in length and complementary to the first complementary sequence of the nucleic acid molecule and a second sequence that is at least 15, at least 20, or at least 30 nucleotides in length and complementary to the second complementary sequence of the nucleic acid molecule, where the first and second sequences are different.

Also provided is a population of the complexes (e.g., at least 1000, at least 10,000, at least 100,000, at least 1M at least 10M, at least 100M, at least 1B, or at least 10B complexes), where the complexes are discrete entities and not hybridized together. In these embodiments, the nucleic acid molecules of each complex comprise a unique identifier sequence in the spacer sequence or the 3' and/or 5' end sequence, wherein the unique identifier sequence is the same in each nucleic acid molecule within a complex but different in different complexes. The identifier sequence can be 6-20 nucleotides in length, but identifier sequences that have a length outside of this range may be used in certain circumstances. In some embodiments, the sequence of the different complexes are the same except for the unique identifier sequence.

Figure 7:
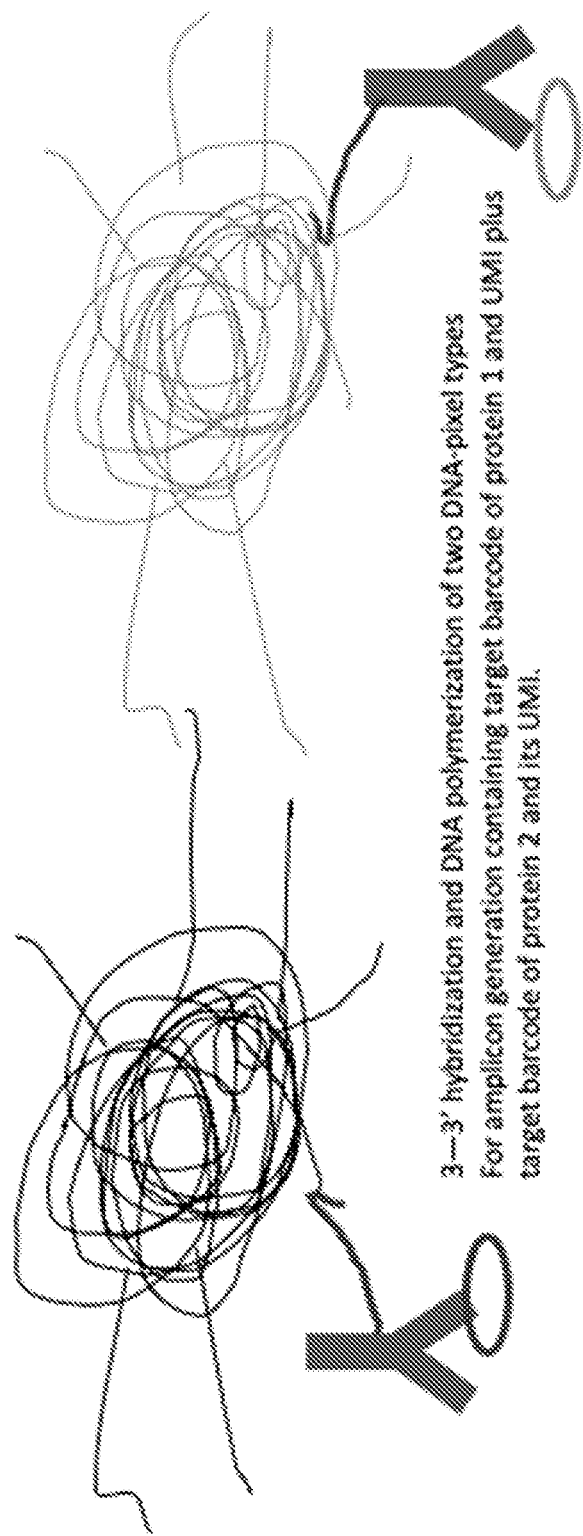
FIG. 7 schematically illustrates how the 3' ends of complexes that are made in situ can hybridize to one another. In these embodiments, a 3' end of one complex can be extended using the sequence of another complex as a template. If the complexes have unique identifiers, then the unique identifier from one complex can be copied into the other. In this embodiment, the extension product should contain two complex identifiers. The sequence of the extension product (which can be amplified out) can be sequenced and the pairs of complex identifiers that are in the extension products provides a way to map the complexes relative to one another.

In some embodiments, the free ends of the complexes in a population may hybridize to one another (as illustrated in FIG. 7), thereby allowing a free end from one complex to be extended using the other as a template.

In some embodiments, the population may contain two types of complexes, where one type of complex has free 5' ends and the other type of complex has free 3' ends. The composition may contain at least 1000, at least 10,000, at least 100,000, at least 1M at least 10M, at least 100M, at least 1B, or at least 10B of each type of complex, where each complex has a unique complex identifier. In these embodiments, the free ends of the complexes do hybridize to one another. For example, the free 3' end sequence may be the same in each of the complexes that have a free 3' end, and the free 5' end sequence may be the same in each of the complexes that have a free 5' end, where the free 3' and 5' end sequences do hybridize to one another. In these latter embodiments, the ends may hybridize to another oligonucleotide. See, e.g., FIG. 5.

The complex described above may be made using the following method. In some embodiments, a complex may be made using the method illustrated in FIG. 2. In these embodiments, the method may comprise: amplifying a circle of nucleic acids 20 by rolling circle amplification (RCA) to make an RCA product 22. As shown, the circle comprises complements of: (i) a first complementary sequence A that, in double stranded form, contains a recognition sequence for a nicking endonuclease; (ii) a spacer sequence B; (iii) a second complementary sequence A' that is complementary to the first complementary sequence; and (iv) an end sequence C (shown as A', B', A and C'). As may be apparent, in this circular molecule bases pair intramolecularly via sequences C and C' to make a dumbbell. In this example, RCA product 22 comprises multiple tandem repeats of the complements of sequences (i)-(iv), and, in each repeat the first complementary sequence and the second complementary sequence hybridize together to form double-stranded region that contains the recognition sequence for the nicking endonuclease, and the end sequence forms a loop. The next step of the method involves (b) digesting the product of step (a) with the nicking endonuclease, to nick the double-stranded region close to the loop and release a free end that comprises the end sequence. This nicking step results in complex 24.

In any embodiment, the complex may be made in situ, meaning that it can be made within or on a cell. In any embodiment, the complex can be made in a cell free environment (although it may be used to assay cells).

In some embodiments, the nicking endonuclease may cleave at the 3' side of the loop, thereby releasing release a free 3' end that comprises a 3' end sequence. Nb.BtsI is an example of a nicking endonuclease that could be used to make free 3' ends, although other enzymes, e.g., Nb.BssSI, Nb.BsrDI, Nb.BsmI or Nb.BbvCI could be used instead.

In other embodiments, the nicking endonuclease may be at the 5' side of the loop, thereby releasing release a free 5' end that comprises a 5' end sequence. Nt.AlwI is an example of a nicking endonuclease that could be used to make free 5' ends, although other enzymes, e.g., Nt.BsmAI, Nt.BstNBI, Nt.BspQI or Nt.CviPII could be used instead.

A method for making a complex that contains both free 3' ends and free 5' ends is illustrated in FIG. 3. In this method, an oligonucleotide can be hybridized to the spacer sequence (the loop) to produce a double-stranded recognition site for restriction enzyme or the distal end of the spacer sequence may contain a hairpin that contains a double-stranded recognition site for restriction enzyme. Either way, a product shown in FIG. 3 can be produced and then digested by a restriction enzyme, thereby resulting in a complex that has both free 3' ends and free 5' ends.

Figure 9:
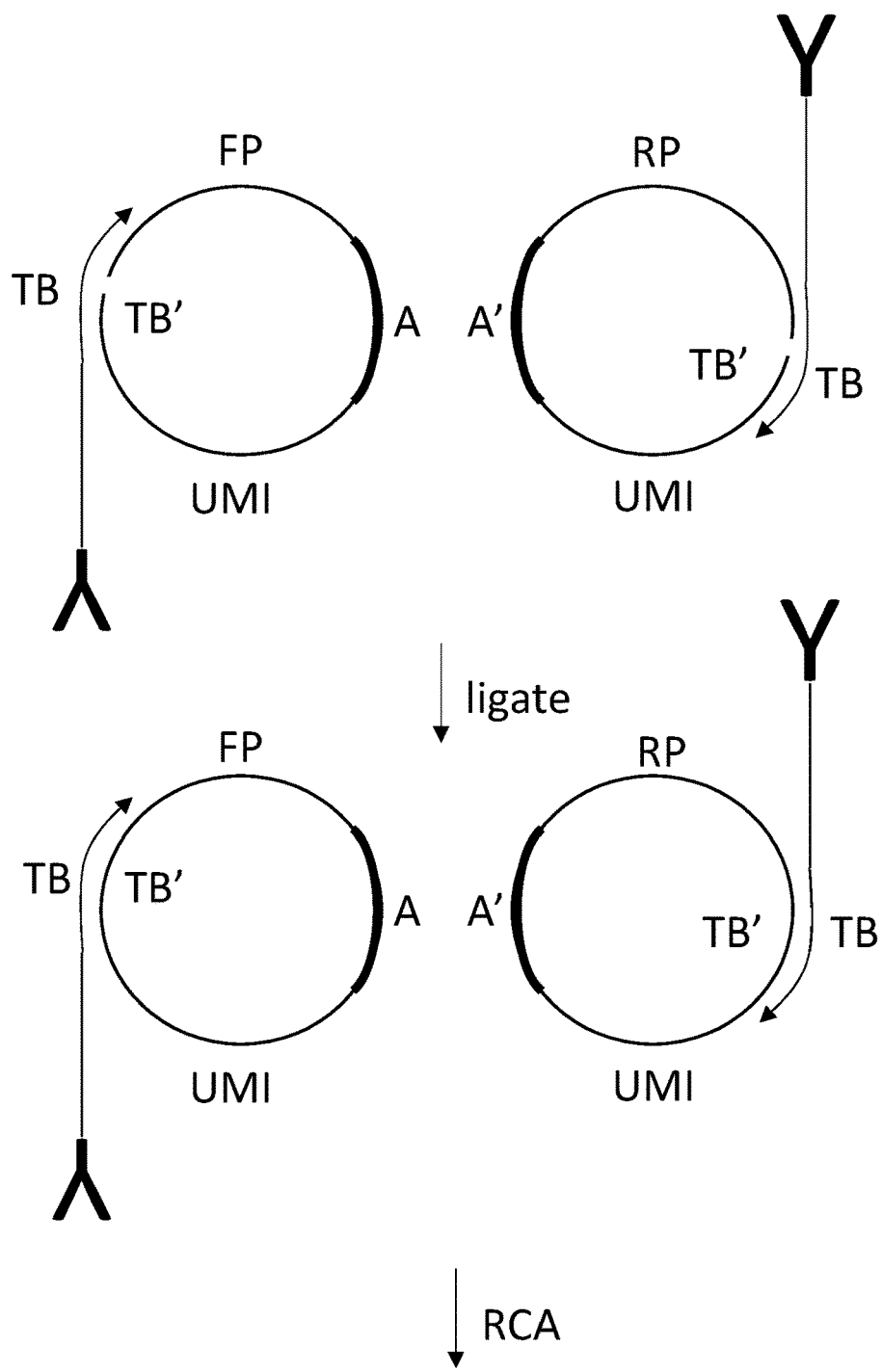
FIG. 9 schematically illustrates an alternative probe system.
Figure 11:
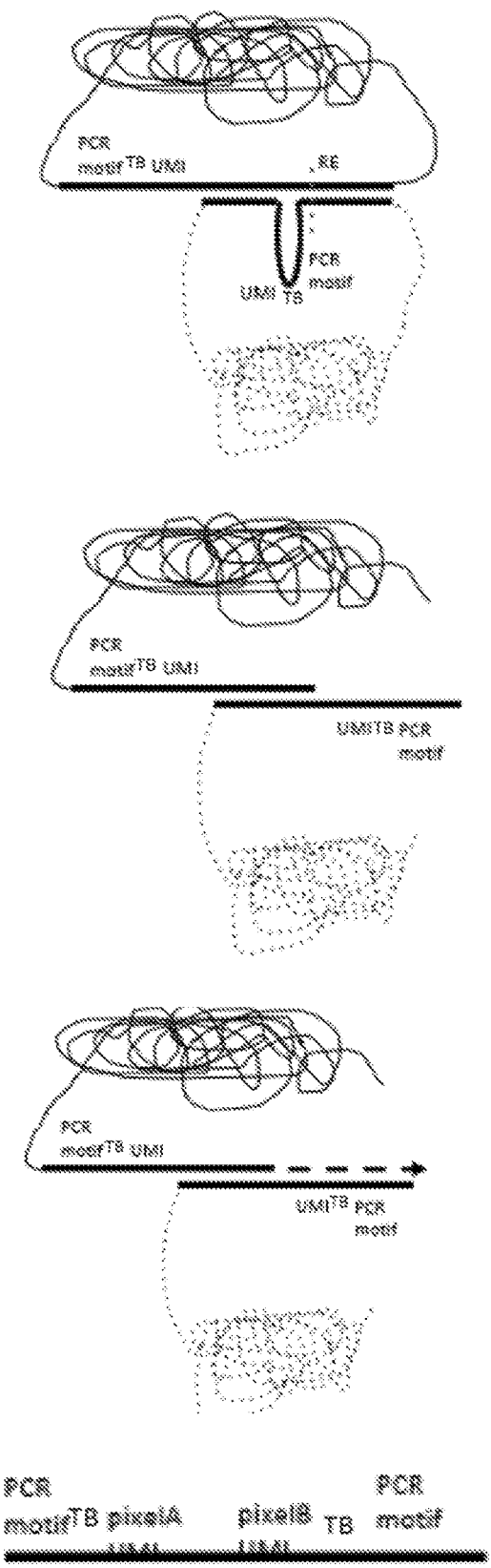
FIG. 11 illustrates how the alternate embodiment shown in FIG. 9 can be used to generate products that have pairs of unique RCA identifier sequences.

Certain embodiments are illustrated in FIGS. 9-11. These embodiments may be particularly used to map RCA products that have been made in situ. As shown in FIG. 9, the probe system may be composed of different conjugates that are composed of binding agents (e.g., antibodies) that are linked to primers, similar to those described above, where in each conjugate the primer has a target barcode (TB), i.e., a target identifier sequence that identifies the binding agent to which it is bound, or the epitope to which the binding agent binds. In the embodiment shown in FIG. 9, the binding agents may be bind to different epitopes or the same epitope. RCA products can be produced in situ using a variety of different methods, see, e.g., Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993), or Schweitzer et al (Curr. Opin. Biotech 2001 12:21-27), which are incorporated by reference herein. RCA products can also be made in situ from probes hybridizing to RNA (see, e.g., Wu S et al Communications Biology 1 2018 209). In some embodiments, the circles of nucleic acid may be made by a ligation assay that joins the end of a linear molecule using the primers as a splint. For example, in some embodiments, the circles or their precursor linear molecules may hybridize to the primers via the TB sequence (as shown in FIG. 9). In other embodiments, the primer may hybridize to a different sequence in the circle.

In these embodiments and as shown in FIG. 9, some of the template circles or their linear precursors have sequence A, a forward primer (FP) sequence, a UMI as well as a sequence that hybridizes to TB (i.e., TB'), whereas the remainder of the template circles or their linear precursors have sequence A', a forward primer (RP) sequence, a UMI as well as a sequence that hybridizes to TB. Other arrangements of sequences are possible. In these embodiments, sequences A and A' are complementary sequence of at least 8, at last 10 or at least 15 nucleotides, e.g., 15-50 nucleotides in length. In some embodiments, the antibody-primer conjugates may be bound to the sample and, after the antibodies are bound, linear or circular oligonucleotides may be hybridized to the sample.

In some embodiments, the first or second complementary sequences (i.e., A and A') may be a sequence that, in double stranded form, contains a recognition sequence for a nicking endonuclease, such that when A and A' hybridize to produce a duplex, the duplex contains a recognition sequence of a nicking endonuclease.

After amplification by RCA, the RCA products have sequences (A and A') that can hybridize to one another such that the RCA products, when hybridized together, form a series of bubbles, as illustrated in FIG. 10. As illustrated on the left-hand side of FIG. 10, the double-stranded parts of the hybridized products can be nicked by the nicking endonuclease to produce free 3' or free 5' ends or, alternatively (and as shown on the right-hand side of FIG. 10), oligonucleotides may by hybridized RCA products, where the oligonucleotides hybridize to produce a restriction site that can be cleaved by a restriction endonuclease. Either way, the sequences can be designed such that after cleavage the 3' ends of the double stranded parts of the duplex can be extended by a polymerase, thereby resulting in a primer extension product that contains unique RCA identifier sequences from two RCA products. Moreover, as illustrated, because the primer extension product should contain two target barcodes as well as binding sites for forward and reverse primers, amplicons that contain two target barcodes and two unique RCA identifier sequences can be readily amplified after primer extension. FIG. 11 illustrates an embodiment of this method in more detail. In these embodiments, one RCA product acts as a splint to hold the other complex together.

Figure 12:
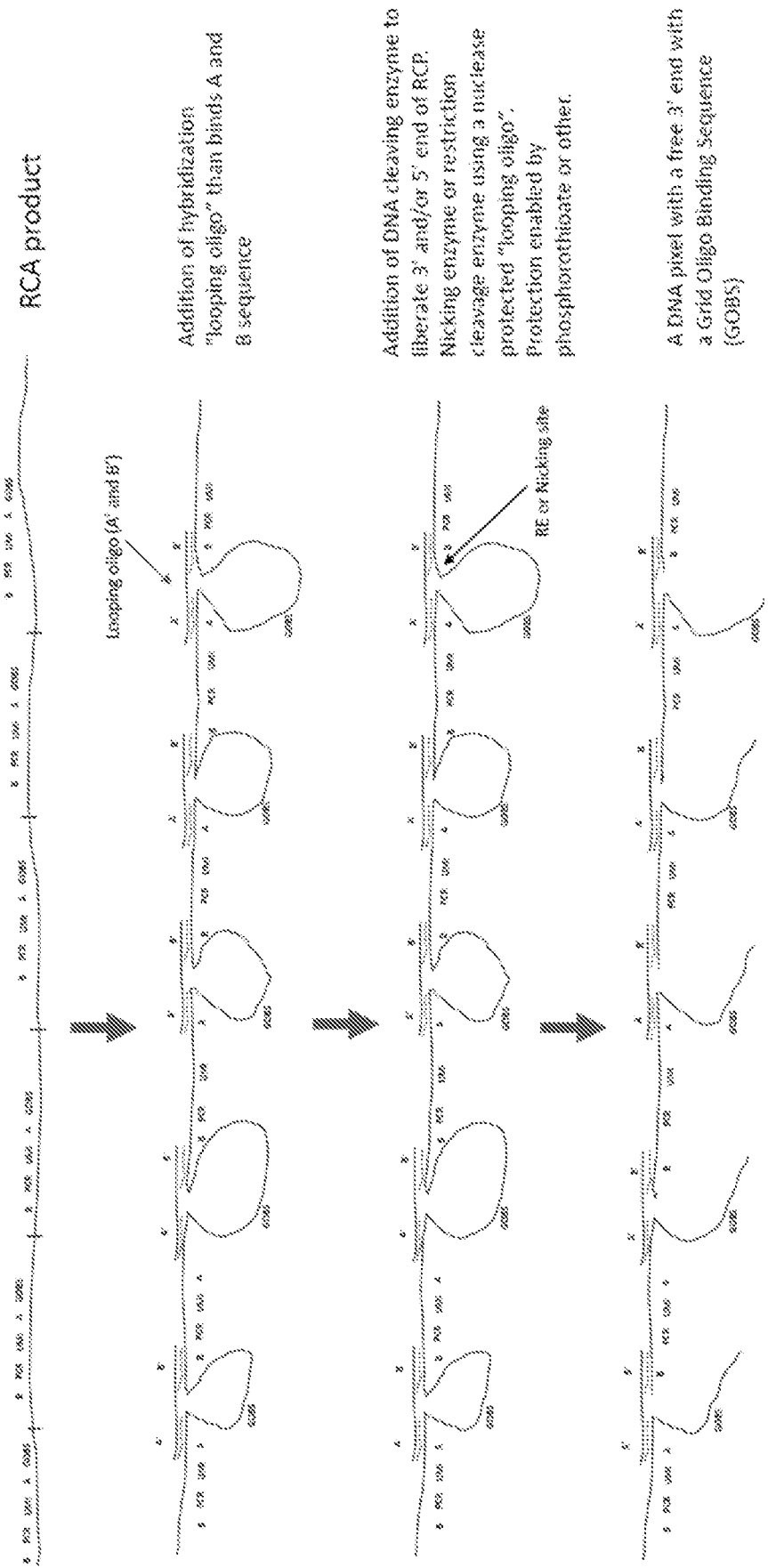
FIG. 12 illustrates how a complex can be produced using a splint oligonucleotide.

A method that for making a complex that is held together by a splint oligonucleotide is shown in FIG. 12. As illustrated, this complex may be made by (a) amplifying a circle of nucleic acid by rolling circle amplification (RCA) to make an RCA product, wherein the circle comprises complements of: a first complementary sequence that, in double stranded form, contains a recognition sequence for a nicking endonuclease or restriction endonuclease; a spacer sequence; a second complementary sequence; and an end sequence, wherein the RCA product comprises multiple tandem repeats of those sequences (sequences (i)-(iv), respectively). A splint oligonucleotide (referred to as a "looping oligonucleotide" in the figure) that contains a first sequence (A') that is complementary to and hybridizes with the first complementary sequence and a second sequence (B') that is complementary to and hybridizes with the second complementary sequence is hybridized with the RCA product, thereby producing a product that contains a series of loops that are joined together by regions that comprise double strands. In this step of the method a splint oligonucleotide hybridizes to the first and second complementary sequences, i.e., (i) and (iii) but not the spacer or end sequences, i.e., sequences (ii) and (iv), in the RCA product, to produce loops. As illustrated, this product is digested with the nicking endonuclease or restriction endonuclease, to nick sequence (i) or (iii) close to the loop and release a free end that comprises the end sequence. In some embodiments, a nicking endonuclease may be used, many examples of which are known and some of which are listed above. In these embodiments, the splint oligonucleotide can be designed to contain at least one uncleavable linkage so that the double stranded region is recognized by a restriction endonuclease, but only one of the strands is actually cleaved, thereby resulting in a nick that releases the 5' or 3' end. In any embodiment, cleavage can be at the 3' side of the loop, thereby releasing a free 3' end that comprises a 3' end sequence. In any embodiment, cleavage can be at the 5' side of the loop, thereby releasing a free 5' end that comprises a 5' end sequence As with other embodiments and as illustrated in FIG. 12, the spacer sequence or the end sequence may comprise a unique identifier sequence and the method comprises amplifying a population of the circles of nucleic acid to produce a population of RCA products, and digesting the products with the nicking endonuclease or restriction endonuclease to produce a plurality of the complexes, wherein each complex has a different unique identifier sequence.

In some embodiments, the spacer sequence or the end sequence comprises a unique identifier sequence. In these embodiments, the method comprises amplifying a population of the circles of nucleic acid to produce a population of RCA products, and digesting the products with the nicking endonuclease to produce a plurality of the complexes, wherein each complex has a different a unique identifier sequence. In these embodiments, the initial circles have a unique identifier, which is copied into the RCA products. Amplification of circularized oligonucleotides that have a degenerate sequence produces a population of RCA products that each have a unique identifier (i.e., a sequence that is different from the other RCA products in the population). Methods for generating RCA products that have unique identifiers are described in Wu et al (Nat. Comm. 2019 10: 3854) and US20160281134, for example, and are readily adapted for use herein. In these embodiments, the RCA product can be made by, e.g., synthesizing initial oligonucleotides that have a degenerate sequence, circularizing the initial oligonucleotides using a splint, and amplifying the circularized oligonucleotides by RCA. In some embodiments, the initial oligonucleotides may contain a degenerate (e.g., random) sequence of 6-10 nucleotides, or even more random nucleotides dependent on the number of unique RCA products required.

Also provided is an assay that uses a complex described above. In general terms, the method may comprise hybridizing a complex with a target polynucleotide, wherein the 3' and/or 5' end sequence of a nucleic acid molecule of the complex hybridizes with the target polynucleotide to produce a duplex; extending (either by ligation, addition by a polymerase potentially by a gap-fill/ligation reaction) the nucleic acid molecule or the target polynucleotide using the other member of the duplex as a template to produce an extension product; and sequencing the extension product. As would be apparent, the 3' and/or 5' end sequence of the nucleic acid molecule may have at least 8, at least 10 or at least 15 nucleotides of complementarity with the target sequence in this embodiment. In some embodiments, the complex and the target sequence (which may be another complex) may be designed to contain primer binding sites or complements thereof, thereby allowing the extension products to be amplified by PCR. As would be apparent, the unique identifier sequences can also be amplified and sequenced in this reaction, thereby allowing one to identify which complexes are adjacent.

Figure 4:
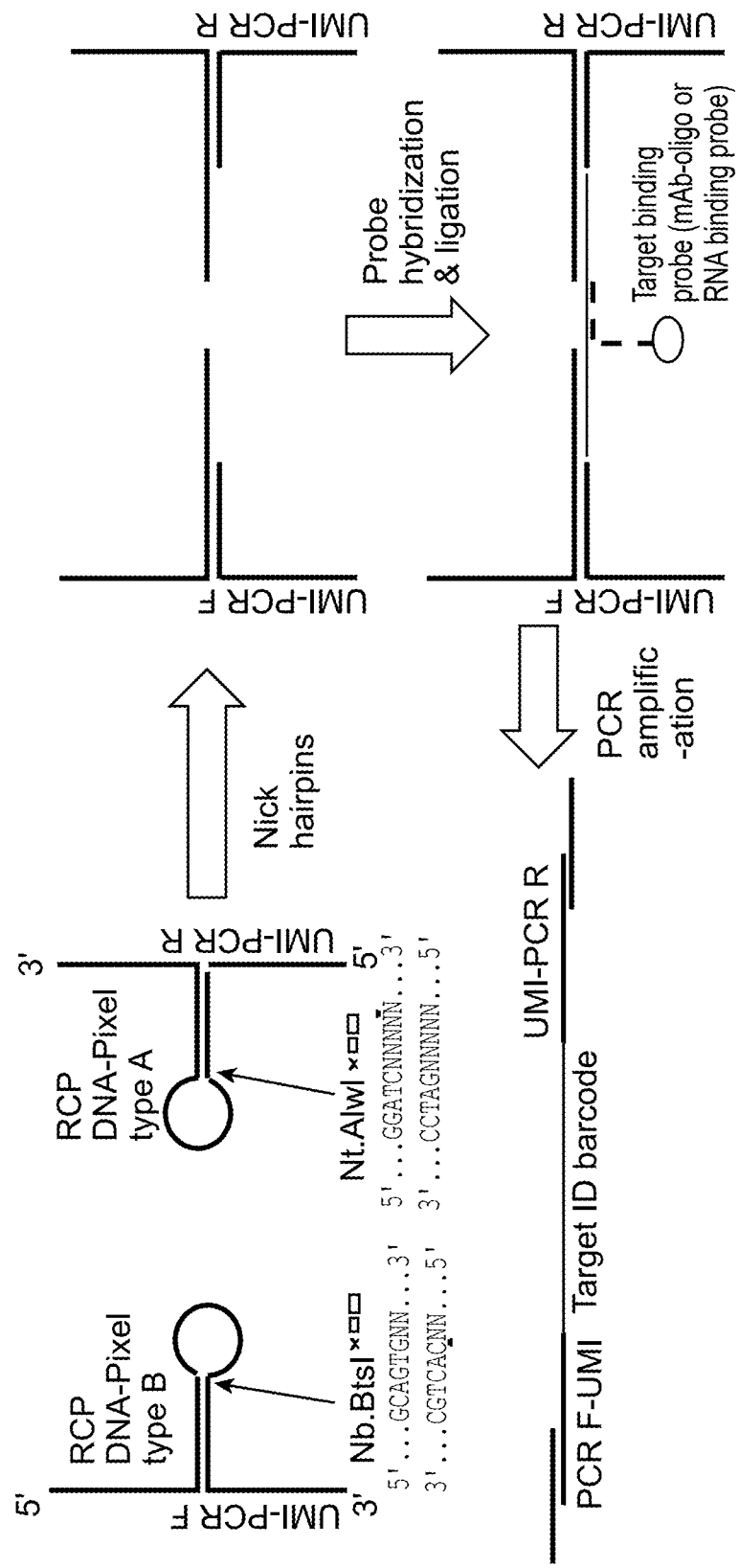
FIG. 4 schematically illustrates a strategy for making complexes that have free 3' ends and complexes that have free 5' ends. In this method, the complexes may be hybridized to an oligonucleotide that contains a target identification sequence (which, in this embodiment, is attached to an antibody or oligonucleotide probe and the target identification sequence identifies the epitope/sequence to which the antibody or probes bind) and then united via a gap-fill/ligation reaction, thereby joining the unique identifiers from adjacent complexes pixels with a target identifier. In this example, the complexes also contain PCR primer sites which allow the product to be amplified. Nt.Alwl, under RCP DNA-Pixel type A, from top to bottom SEQ ID NO: 47-48
Figure 5:
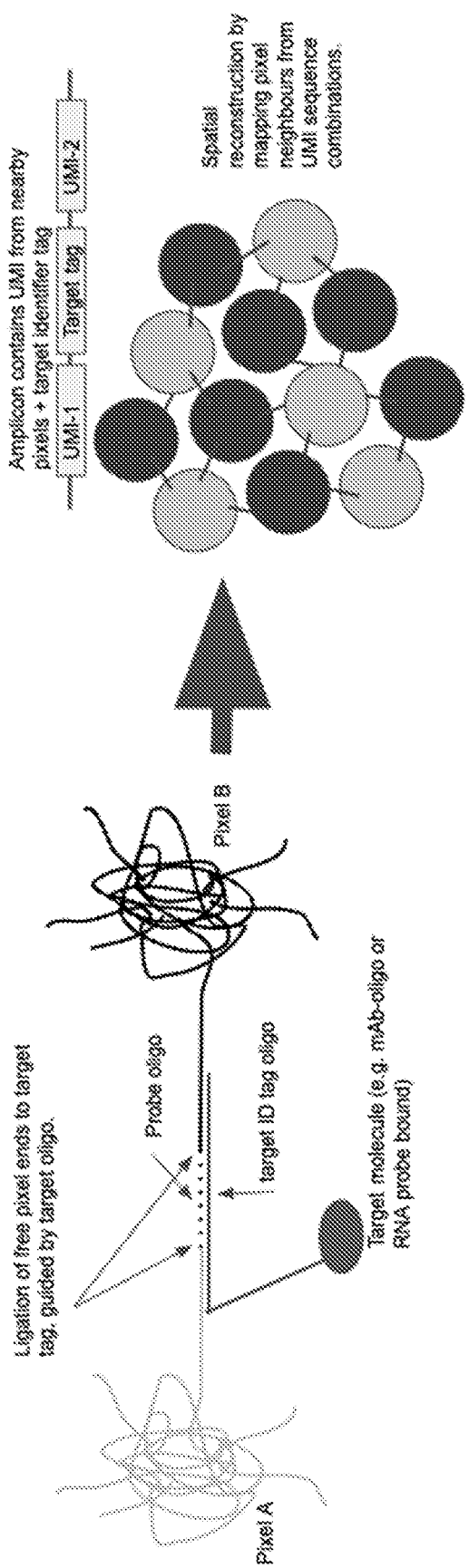
FIG. 5 schematically illustrates one way by which binding events can be mapped using complexes having free 3' and/or 5' ends. In this example, the target molecule may be bound to a cell, and an identifier from an oligonucleotide that is tethered to that molecule may be copied by extension of the 3' end of a complex. In this example, the resulting product contains the identifiers from two complexes (UMI-1 and UMI-2) as well as the identifier for the target. As shown, the complexes can be mapped relative to one another in a pairwise way, and the sites to which the target binds can be mapped onto the map of complexes.

In some cases, two sets of complexes may be produced, one with free 3' ends and the other with free 5' ends. In some cases, these ends may be complementary such that the complexes can bind together and the ends can be extended, if desired. In other cases, the complexes hybridize to the same oligonucleotide (e.g., an oligonucleotide that is linked to a binding agent such as an antibody, aptamer or nucleic acid probe). In these embodiments, the free 3' and 5' ends can be ligated together using the oligonucleotide as a splint. Alternatively, any gap between the 3' end of one molecule and the 5' end of another molecule can be filled in by a primer extension/ligation reaction that uses the oligonucleotide as a template (see, e.g., Mignardi et al, Nucleic Acids Res. 2015 43: e151) In this embodiment, the oligonucleotide may contain an identifier sequence that identifies a binding agent to which it is tethered, where the binding agent identifier sequence is copied in the primer-extension/ligation reaction. In this embodiment, a product containing two complex identifier sequences as well as a binding agent identifier sequence can be amplified, thereby allowing one to identify adjacent complexes as well as the binding agent to which they are bound. This embodiment is illustrated in FIGS. 4 and 5.

In some embodiments, two or more (e.g., at least 50 or at least 10) nucleic acid molecule of the same complex may hybridize with separate target polynucleotides to produce a plurality of duplexes. In this method, the method may comprise extending the two or more nucleic acid molecules or the separate target polynucleotides using the other members of the duplexes as a template to produce extension products and sequencing the extension products. As with the example above, two sets of complexes may be produced, one set with free 3' ends and the other set with free 5' ends. Such compositions can be used in a variety of proximity assays.

For example, the complexes may be mapped relative to one another if two complex identifiers are added to the same molecule. The map produced by the method may be a three-dimensional map or a two-dimensional map, depending on how the method is implemented. For example, if the complexes products are immobilized within cells (e.g., produced in situ in cells) then the map produced may be three dimensional. In other embodiments, e.g., if the complexes are immobilized on one or more surfaces (e.g., the surface of one or more cells that may be in suspension or mounted on a support), then the map produced by the method may be two dimensional. While the method can be applied to cells (as described below) the method can be adapted to map adjacent complexes that are immobilized on any surface, e.g., a glass slide that may have a tissue blot, or a western blot, etc. Likewise, although the complexes can be anchored to sites in or on cells or on a surface via an antibody (e.g., an antibody that is conjugated to an oligonucleotide that has a sequence that is complementary to a sequence in a complex), the complexes can be immobilized via any type of interaction, e.g., covalent or non-covalent interactions, directly or indirectly. For example, in some embodiments, the complexes may be bound to the cell via a binding agent (e.g., an aptamer, an antibody or an oligonucleotide, etc.), where the binding agent binds to a sequence in the complexes and a site in a cell or on the surface of the one or more cells. In some embodiments, the complexes may be immobilized via hybridization to an oligonucleotide that also hybridizes to a nucleic acid (e.g., to a cellular RNA) or the RCA products may be immobilized non-covalently to a site via an electrostatic interactions, via a streptavidin/biotin interaction, or by a covalent linkage (e.g., via a click coupling). An example of this reaction and how the complexes can be mapped is illustrated in FIGS. 4 and 5.

In any embodiment, the complexes may be immobilized in or on cells that are in solution, cells that are on a support (e.g., a slide), cells that in a three-dimensional sample of tissue, or cells that are in a tissue section. A sample containing cells that are in solution may be a sample of cultured cells that have been grown as a cell suspension, for example. In other embodiments, disassociated cells (which cells may have been produced by disassociating cultured cells or cells that are in a solid tissue, e.g., a soft tissue such as liver of spleen, using trypsin or the like) may be used. In particular embodiments, the complexes may be immobilized on cells that can be found in blood, e.g., cells that in whole blood or a sub-population of cells thereof. Sub-populations of cells in whole blood include platelets, red blood cells (erythrocytes), and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If cells that are immobilized on a support are used, then then the sample may be made by, e.g., growing cells on a planar surface, depositing cells on a planar surface, e.g., by centrifugation, by cutting a three dimensional object that contains cells into sections and mounting the sections onto a planar surface, i.e., producing a tissue section. In alternative embodiments, the surface may be made by absorbing cellular components onto a surface.

In any embodiment, the method may comprise immobilizing thousands, tens of thousands, hundreds of thousands or at least a million complexes (each having a unique identifier), to a population of cells (e.g., via an antibody) so that on each cell the complexes effectively coat the cells. The complexes may hybridize to other oligonucleotides that are tethered to sites in or on a cell to produce a matrix comprising the complexes. After hybridization, the unique identifier sequences of adjacent complexes can be copied from one complex to another. A physical map of the complexes, as well as the sites to which the complexes bind to the cell, can be constructed based on the sequences that have been copied.

In addition to making a map of the complexes, the method may involve performing a proximity assay between one or more binding agents that are bound to sites in the cells or on the surface of the cells (e.g., antibodies that are bound to cell surface markers on the cells). In these embodiments, a product may contain a pair of unique complex identifier sequences as well as a binding agent identifier sequences. In some embodiments, the binding agent may be an antibody-oligonucleotide conjugate and in other embodiments, the capture agent may be an oligonucleotide probe. In these embodiments, the terms "antibody-oligonucleotide conjugate" and "capture agent that is linked to a oligonucleotide" refers to a capture agent, e.g., an antibody or aptamer, that is non-covalently (e.g., via a streptavidin/biotin interaction) or covalently (e.g., via a click reaction or the like) linked to a single-stranded oligonucleotide in a way that the capture agent can still bind to its binding site. The oligonucleotide and the capture agent may be linked via a number of different methods, including those that use maleimide or halogen-containing groups, which are cysteine-reactive. The capture agent and the oligonucleotide may be linked proximal to or at the 5' end of the oligonucleotide, proximal to or at the 3' end of the oligonucleotide, or anywhere in-between. In some embodiments, the oligonucleotides may be linked to the capture agents by a linker that spaces the oligonucleotide from the capture agents. Oligonucleotides may be linked to capture agents using any convenient method (see, e.g., Gong et al., Bioconjugate Chem. 2016 27: 217-225 and Kazane et al. Proc Natl Acad Sci 2012 109: 3731-3736). In many embodiments, the sequence of an oligonucleotide that is conjugated to a binding agent uniquely identifies the epitope or sequence to which the binding agent binds. For example, if the method is performed using 10 different antibodies, then each antibody is tethered to a different sequence that identifies the epitope to which the antibody binds. This feature allows the method to be multiplexed and, in some embodiments, at least 5, at least 10, at least 20 or at least 50 different antibodies that bind to different markers in or on the surface of a cell can be used in the method. Each antibody is conjugated to a different antibody identifier sequence, and the antibody identifier sequences allow the binding events for a particular antibody to be mapped. Such tagged antibodies are described in, e.g., Wu et al (Nat. Comm. 2019 10: 3854) and US20160281134, and others.

EXAMPLES

The following examples are put forth so as to provide those of ordinary skill in the art with additional disclosure and description of how to make and use the present invention, and are not intended to limit the scope of what the inventors regard as their invention nor are they intended to represent that the experiments below are all or the only experiments performed.

Example 1

Complexes containing free 5' and/or free 3' ends can be made from rolling circle amplification products (RCPs). Such molecules can be manufactured by first circularizing a DNA oligonucleotide containing complements of the complex components, i.e., complements of a first complementary sequence; a spacer sequence; a second complementary sequence that is complementary to the first complementary sequence, and an end sequence, and, if desired, a unique molecular identifier (UMI) sequence (also sometimes called random or degenerate barcode). This circular molecule is amplified by rolling circle replication using a strand-displacing DNA polymerase to make a concatemer of hundreds or thousands of copies of the reverse complement of the circle. As illustrated in FIG. 2, the resulting RCA products contain stem-loop structures (produced by intramolecular hybridization of the first and second complementary sequences) that contains a nicking restriction enzyme site or a restriction enzyme site. Next, a nicking enzyme is added. Depending on the enzyme used and the design of the hairpin, the enzyme should cleave one strand of the stem-loop structure liberating i. a free 3' OH which is still based paired or close to the hairpin, and a free 5' P or ii. a free 5' P which is still based paired or close to the hairpin, and ii. a free 3' OH. These ends can be designed to be either single stranded or double stranded depending on the molecular biology reaction to be used for uniting the UMI of the DNA-pixel with the target barcoded of the probing agent, such as an antibody with a DNA-tag or an RNA binding probe with a DNA-tag.

As an alternative approach to liberating 3' and/or 5' ends while maintaining DNA-pixel integrity and not dissociating into monomer units is to use a stable stem and a standard restriction enzyme that cleaves both strands of dsDNA in the loop structure as shown in FIG. 3. This version uses a standard restriction enzyme that cleaves both strands of a double stranded DNA molecule and not just one strand as in a nicking restriction enzyme.

Example 2

The principles of one embodiment of a method for mapping binding events are illustrated in FIG. 4. In this example, two types of RCA products are produced, which are processed into two types of complexes, one having free 3' ends and the other having free 5' ends. The two types of RCA product are label as Type A and Type B in this figure and only one unit of each of the RCA products is shown. In this example, the nicking enzymes release the loop structure of the stem-loop while the complex is held together by hybridization. In the assay, the 3' free pixel can be united with the 5' free pixel via the target binding probe sequence, which results in a product that can be amplified by PCR to produce an amplicon containing a forward binding site, Pixel B UMI, target BC, Pixel A UMI, and a reverse primer binding site.

Once nicked by the nicking enzyme, these complexes are not covalently held together but only held together by DNA hybridization. In order for the stem-loop based DNA-pixel to be stable and intact throughout the assays, the stem-loop structure should be to sufficiently stable up until the PCR step. The length of the stem-loop can be varied with increasing length providing greater stability and/or the GC content of the stem-loop could be increased. If necessary, a stabilizing oligonucleotide can be added to bind to the sequences directly adjacent to the stem-loop structure forming a tripartite complex further increasing the DNA-pixel stability, as illustrated in FIG. 8.

Example 3

One way by which the positions of binding events can be mapped relative to one another is shown in FIG. 5. In this example, target binding oligonucleotides (which are linked to an antibody or an oligonucleotide probe, for example)

template a gap-fill/ligation reaction that unites the identifiers from complexes that are near one another, at the same time, inserting the target identification tag into the amplicon (in the gap-fill reaction). The resulting matrix of complexes are linked by the target identification tags of underlying binding events, and the complex identifier sequences and the target identification tags in the amplicons can be used to deconvolute and to build a map of binding events.

Example 4

The complexes may also be made in situ. Several technologies exist that make RCA products in situ in a target presence dependent way for RNA and/or protein detection, including but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993), and Schweitzer et al (Curr. Opin. Biotech 2001 12:21-27), which are incorporated by reference herein. RCA products can be made in situ from probes hybridizing to RNA (see, e.g., Wu S et al Communications Biology 1 2018 209).

Figure 6:
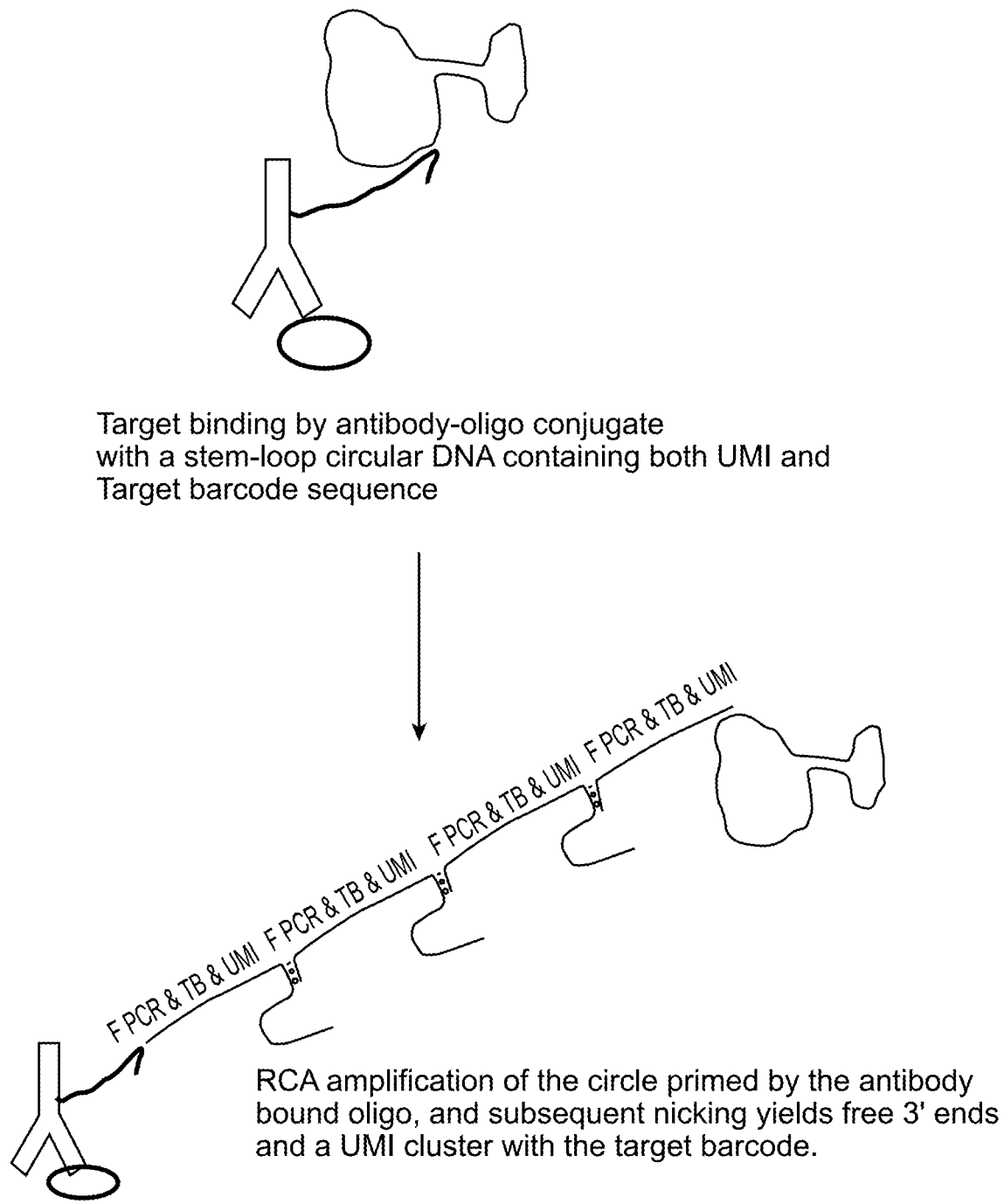
FIG. 6 schematically illustrates how complexes can be made in situ.

These types of in situ-produced RCA products can be designed to incorporate the described stem-loop structure which is then nicked in situ by an enzyme liberating a free 3' and/or 5' end capable of uniting with an adjacent DNA-pixel from another target binding event as seen in FIGS. 4 and 5. The circular template for the in situ RCA can be designed to include both the target biomolecule identity tag and the UMI. The DNA sequence mesh includes information on the target protein identity and their relative locations from the UMI combinations. FIG. 6 shows in situ RCA generating a repeat concatemer of target protein identity, UMI, and Forward PCR primer. FIG. 7 shows different sequence based DNA-pixels used in order to ensure that all uniting events are inter-pixel and not intra-pixel, thus improving the informatic sequence mesh formation.

Example 5

Methods

Probe circularization and Rolling circle amplification: Probe oligo (1 or 2) was circularized using T4 DNA ligase in 50 µl reactions containing 100 nM probe oligo, 1 mM ATP, 200 U T4 DNA ligase and a reaction buffer containing 33 mM Tris-acetate, 10 mM Mg-acetate, 66 mM K-acetate, 1 mM DTT, and 0.1% Tween20. The reaction was incubated at 37° C. for 30 minutes.

Non-circularized probes were digested by adding 10 U Exonuclease I and 100 U exonuclease III to each reaction following ligation. The exonuclease digestion was performed for 30 min at 37° C., followed by heat inactivation at 85° C. for 20 min.

RCA primer oligo (3 or 4) was added to each reaction after exonuclease digestion to a concentration of 100 nM and was allowed to hybridize to the circularized probes by incubation at 37° C. for 20 min.

Rolling circle amplification was performed in 75 µl reactions containing 1 nM circularized probe, 0.75 mM of each dNTP, 7.5 U phi29 DNA polymerase, 0.1 mg/ml BSA in the same reaction buffer as used during probe circularization. The reaction was incubated for 30 min at 37° C., followed by heat inactivation at 65° C. for 10 min.

RCA products were nicked to liberate 3' (probe 1) or 5' ends (probe 2), using nicking endonuclease Nt.AlwI for probe 1 and Nb.BtsI for probe 2. The nicking reaction was performed by adding 15 U of each nicking enzyme to each 75 µl RCA reaction. The reactions were incubated for 2.5 h at 37° C. Nicked RCA products were stored at 4° C. until use.

Binding of cell surface target markers by antibody-DNA conjugates: Raji cells were aspirated from a T75 flask and spun down at 300×g for 5 min. Cells were counted and cell suspension corresponding to 1 M cells were taken. Cells were washed twice in FACS buffer (2% FBS, 2 mM EDTA in 1×PBS). Cells were blocked with FcR blocking agent and spun down to remove the supernatant.

A pool of 20 TotalSeq B (Biolegend Inc) antibody-oligonucleotide conjugates targeting various immune cell markers (CD3, CD4, etc) (oligo 7-26) with a corresponding linker or so-called grid-oligo hybridized to them (oligo 27-46) in order to enable ligation was added to the cells at a antibody-conjugate concentration of 5 µg/ml of each conjugate and incubated for 30 min on ice. The conjugate-stained cells were washed twice with 300 µl FACS buffer after which the cells were spun down, supernatant removed and 250 µl of 1% PFA was added to fix the sample. After 10 minute incubation at RT, the fixation was quenched by addition of 12.5 µl of 2.5 M Glycine, followed by a wash with 250 µl of 125 mM Glycine in PBS. After another wash in PBS cells were resuspended in PBS and stored at +4° C. until use.

Ligation of nicked RCA products to linker(grid) oligo (pix40): An aliquot of conjugate-stained and fixated cells corresponding to 20,000 cells were transferred to a PCR tube. A 30 µl reaction mix containing 10 µl each of nicked RCA products originating from probe oligo 1 and 2 and 10 µl of a hybridization buffer were added to the bead tube. The buffer composition of the final 30 µl reaction was 800 mM NaCl, 15 mM MgCl$_2$, 10 mM Tris-HCl (pH 8). The Reaction was incubated for 30 min at 37° C.

A washing step was performed by adding 100 µl PBS with 0.05% Tween20, pelleting the cells by centrifugation at 500×g for 2 min, and removing the wash buffer.

A 30 µl ligation master mix containing 1 mM ATP, 480 U T4 ligase in a buffer comprising 33 mM Tris-acetate, 10 mM Mg-acetate, 66 mM K-acetate, 1 mM DTT, and 0.1% Tween20 was added to the washed cell pellet. After resuspension, the reaction was incubated for 30 min at 37° C. The reaction was again washed once and resuspended in 50 µl storage buffer consisting of 1 mM EDTA, 50 mM NaCl and 20 mM Tris-HCl, pH 8.

The cell suspension was diluted to a concentration of 20 cells per ul and a 5 µl sample was PCR amplified in a reaction with 0.2 mM dNTPs, 0.4 uM each of Fwd and Rev primers (7, 8), 1 U Phusion DNA polymerase and 1× of Phusion HF PCR buffer.

PCR was performed for 15 cycles at 98° C. denaturation for 1 min, followed by 15 cycles of 10 sec denaturation at 98° C., 30s annealing at 60° C., 40s at 72° C. before a final extension at 72° C. for 5 min.

The PCR product was finally purified using Ampure XP beads following the manufacturer's instructions but using a bead-to-sample ratio of 1.2. The purified PCR product was quantified using a Qubit fluorometer and sequenced on an Illumina NextSeq 2000 sequencer.

Each sequencing read contained the two DNA pixel barcodes incorporated during the ligation step of the assay. DNA pixel barcode sequences were extracted from each read and the list of DNA pixel barcodes was used as an edge list in the construction of an undirected graph, with each component of the graph representing a single cell.

Oligos Used:

| SEQ ID NO: | Name | Sequence |
|---|---|---|
| 1 | D13_PLA | /5Phos/GGATCGCAGCCTAGCGCTGATGATAGCTGCGATCCTCGACGCCTGNNNNNNNNNNNNNNNNNAGATCGGAAGAGCACACGTCTGAACTCCAGTCACCAGGCGTCGA |
| 2 | D13_PLB | /5Phos/TCGACGCCTGTCTTTCCCTACACGACGCTCTTCCGATCTNNNNNNNNNNNNNNNNNCAGGCGTCGATGGCAGTGCGTAGCCTGGGAATACTCGCACTGCCA |
| 3 | D7_PLA_RCA primer | GACGTGTGCTCTTCCGA*T*C*T |
| 4 | D7_PLB_RCA primer | AGATCGGAAGAGCGTCG*T*G*T |
| 5 | Fwd primer | CAAGCAGAAGACGGCATACGAGATAACCGCGGGTGACTGGAGTTCAGACGTGTGCTCTTCCGATCT |
| 6 | Rev primer | AATGATACGGCGACCACCGAGATCTACACTCTTTCCCTACACGACGCTCTTCCGATCT |
| 7 | CD45_TSeqB | GTGACTGGAGTTCAGACGTGTGCTCTTCCGATCTNNNNNNNNNNNTCCCTTGCGATTTACNNNNNNNNNGCTTTAAGGCCGGTCCTAGC*A*A |
| 8 | CD3_TSeqB | GTGACTGGAGTTCAGACGTGTGCTCTTCCGATCTNNNNNNNNNNNTATCCCTTGGGATGGNNNNNNNNNGCTTTAAGGCCGGTCCTAGC*A*A |
| 9 | CD19_TSeqB | GTGACTGGAGTTCAGACGTGTGCTCTTCCGATCTNNNNNNNNNNNCTGGGCAATTACTCGNNNNNNNNNGCTTTAAGGCCGGTCCTAGC*A*A |
| 10 | IgG1ctrl_TSeqB | GTGACTGGAGTTCAGACGTGTGCTCTTCCGATCTNNNNNNNNNNNGCCGGACGACATTAANNNNNNNNNGCTTTAAGGCCGGTCCTAGC*A*A |
| 11 | CD20_TSeqB | GTGACTGGAGTTCAGACGTGTGCTCTTCCGATCTNNNNNNNNNNNTTCTGGGTCCCTAGANNNNNNNNNGCTTTAAGGCCGGTCCTAGC*A*A |
| 12 | CD69_TSeqB | GTGACTGGAGTTCAGACGTGTGCTCTTCCGATCTNNNNNNNNNNNGTCTCTTGGCTTAAANNNNNNNNNGCTTTAAGGCCGGTCCTAGC*A*A |
| 13 | HLA-DR_TSeqB | GTGACTGGAGTTCAGACGTGTGCTCTTCCGATCTNNNNNNNNNNNAATAGCGAGCAAGTANNNNNNNNNGCTTTAAGGCCGGTCCTAGC*A*A |
| 14 | CD8_TSB | GTGACTGGAGTTCAGACGTGTGCTCTTCCGATCTNNNNNNNNNNNGCTGCGCTTTCCATTNNNNNNNNNGCTTTAAGGCCGGTCCTAGC*A*A |
| 15 | CD14_TSB | GTGACTGGAGTTCAGACGTGTGCTCTTCCGATCTNNNNNNNNNNNCAATCAGACCTATGANNNNNNNNNGCTTTAAGGCCGGTCCTAGC*A*A |
| 16 | IgG2isoCtrl_TSB | GTGACTGGAGTTCAGACGTGTGCTCTTCCGATCTNNNNNNNNNNNATATGTATCACGCGANNNNNNNNNGCTTTAAGGCCGGTCCTAGC*A*A |
| 17 | CD45RA_TSB | GTGACTGGAGTTCAGACGTGTGCTCTTCCGATCTNNNNNNNNNNNTCAATCCTTCCGCTTNNNNNNNNNGCTTTAAGGCCGGTCCTAGC*A*A |
| 18 | CD45RO_TSB | GTGACTGGAGTTCAGACGTGTGCTCTTCCGATCTNNNNNNNNNNNCTCCGAATCATGTTGNNNNNNNNNGCTTTAAGGCCGGTCCTAGC*A*A |
| 19 | CD62L_TSB | GTGACTGGAGTTCAGACGTGTGCTCTTCCGATCTNNNNNNNNNNNGTCCCTGCAACTTGANNNNNNNNNGCTTTAAGGCCGGTCCTAGC*A*A |
| 20 | CD82_TSB | GTGACTGGAGTTCAGACGTGTGCTCTTCCGATCTNNNNNNNNNNNTCCCACTTCCGCTTTNNNNNNNNNGCTTTAAGGCCGGTCCTAGC*A*A |
| 21 | CD7_TSB | GTGACTGGAGTTCAGACGTGTGCTCTTCCGATCTNNNNNNNNNNNTGGATTCCCGGACTTNNNNNNNNNGCTTTAAGGCCGGTCCTAGC*A*A |
| 22 | CD70_TSB | GTGACTGGAGTTCAGACGTGTGCTCTTCCGATCTNNNNNNNNNNNCGCGAACATAAGAAGNNNNNNNNNGCTTTAAGGCCGGTCCTAGC*A*A |
| 23 | CD72_TSB | GTGACTGGAGTTCAGACGTGTGCTCTTCCGATCTNNNNNNNNNNNCAGTCGTGGTAGATANNNNNNNNNGCTTTAAGGCCGGTCCTAGC*A*A |
| 24 | CD162_TSB | GTGACTGGAGTTCAGACGTGTGCTCTTCCGATCTNNNNNNNNNNNATATGTCAGAGCACCNNNNNNNNNGCTTTAAGGCCGGTCCTAGC*A*A |
| 25 | CD26_TSB | GTGACTGGAGTTCAGACGTGTGCTCTTCCGATCTNNNNNNNNNNNGGTGGCTAGATAATGNNNNNNNNNGCTTTAAGGCCGGTCCTAGC*A*A |
| 26 | CD63_TSB | GTGACTGGAGTTCAGACGTGTGCTCTTCCGATCTNNNNNNNNNNNGAGATGTCTGCAACTNNNNNNNNNGCTTTAAGGCCGGTCCTAGC*A*A |
| 27 | CD45_TSeqB_linker | /5Phos/CCTAGCGCTGATGATAGTTTGTAAATCGCAAGGGATTTCGTAGCCTGGGAATACTCG |
| 28 | CD3_TSeqB_linker | /5Phos/CCTAGCGCTGATGATAGTTTCCATCCCAAGGGATATTTCGTAGCCTGGGAATACTCG |
| 29 | CD19_TSeqB_linker | /5Phos/CCTAGCGCTGATGATAGTTTCGAGTAATTGCCCAGTTTCGTAGCCTGGGAATACTCG |
| 30 | IgG1ctrl_TSeqB_linker | /5Phos/CCTAGCGCTGATGATAGTTTTTAATGTCGTCCGGCTTTCGTAGCCTGGGAATACTCG |
| 31 | CD20_TSeqB_linker | /5Phos/CCTAGCGCTGATGATAGTTTTCTAGGGACCCAGAATTTCGTAGCCTGGGAATACTCG |
| 32 | CD69_TSeqB_linker | /5Phos/CCTAGCGCTGATGATAGTTTTTAAGCCAAGAGACTTTCGTAGCCTGGGAATACTCG |

| SEQ ID NO: | Name | Sequence |
|---|---|---|
| 33 | HLA-DR_TSeqB_linker | /5Phos/CCTAGCGCTGATGATAGTTTTACTTGCTCGCTATTTTTCGTAGCCTGGGAATACTCG |
| 34 | CD8_TSB_linker | /5Phos/CCTAGCGCTGATGATAGTTTAATGGAAAGCGCAGCTTTCGTAGCCTGGGAATACTCG |
| 35 | CD14_TSB_linker | /5Phos/CCTAGCGCTGATGATAGTTTTCATAGGTCTGATTGTTTCGTAGCCTGGGAATACTCG |
| 36 | IgG2isoCtrl_TSB_linker | /5Phos/CCTAGCGCTGATGATAGTTTTCGCGTGATACATATTTTCGTAGCCTGGGAATACTCG |
| 37 | CD45RA_TSB_linker | /5Phos/CCTAGCGCTGATGATAGTTTAAGCGGAAGGATTGATTTCGTAGCCTGGGAATACTCG |
| 38 | CD45RO_TSB_linker | /5Phos/CCTAGCGCTGATGATAGTTTCAACATGATTCGGAGTTTCGTAGCCTGGGAATACTCG |
| 39 | CD62L_TSB_linker | /5Phos/CCTAGCGCTGATGATAGTTTTCAAGTTGCAGGGACTTTCGTAGCCTGGGAATACTCG |
| 40 | CD82_TSB_linker | /5Phos/CCTAGCGCTGATGATAGTTTAAAGCGGAAGTGGGATTTCGTAGCCTGGGAATACTCG |
| 41 | CD7_TSB_linker | /5Phos/CCTAGCGCTGATGATAGTTTAAGTCCGGGAATCCATTTCGTAGCCTGGGAATACTCG |
| 42 | CD70_TSB_linker | /5Phos/CCTAGCGCTGATGATAGTTTCTTCTTATGTTCGCGTTTCGTAGCCTGGGAATACTCG |
| 43 | CD72_TSB_linker | /5Phos/CCTAGCGCTGATGATAGTTTTATCTACCACGACTGTTTCGTAGCCTGGGAATACTCG |
| 44 | CD162_TSB_linker | /5Phos/CCTAGCGCTGATGATAGTTTGGTGCTCTGACATATTTTCGTAGCCTGGGAATACTCG |
| 45 | CD26_TSB_linker | /5Phos/CCTAGCGCTGATGATAGTTTCATTATCTAGCCACCTTTCGTAGCCTGGGAATACTCG |
| 46 | CD63_TSB_linker | /5Phos/CCTAGCGCTGATGATAGTTTAGTTGCAGACATCTCTTTCGTAGCCTGGGAATACTCG |

Results

Figure 13:
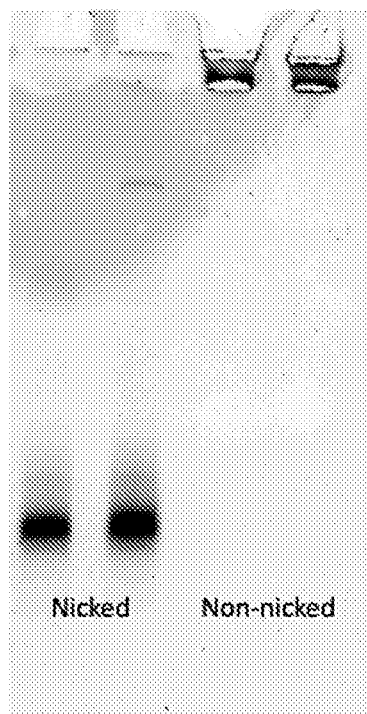
FIG. 13 shows a denaturing TBE-urea gel on nicked and non-nicked RCA products.

Validation of RCA product formation: Padlock probes (1-2) used as templates for RCA were designed to contain a stem-loop structure, including a nicking enzyme restriction site within the stem region. Upon restriction enzyme digestion of RCA products, the loop is cleaved, liberating a protruding 3' or 5' end depending on the template used. Nicked or non-nicked pixels were run on a denaturing TBE-Urea PAGE gel to confirm that a RCA product had been formed and that RCA products could be nicked at high efficiency. A complete nicking of all restriction sites within RCA products should form a distinct band corresponding to the length of the template oligo used for RCA, whereas non-nicked RCA products should remain at the top of the gel due to their size (FIG. 13).

Figure 14:
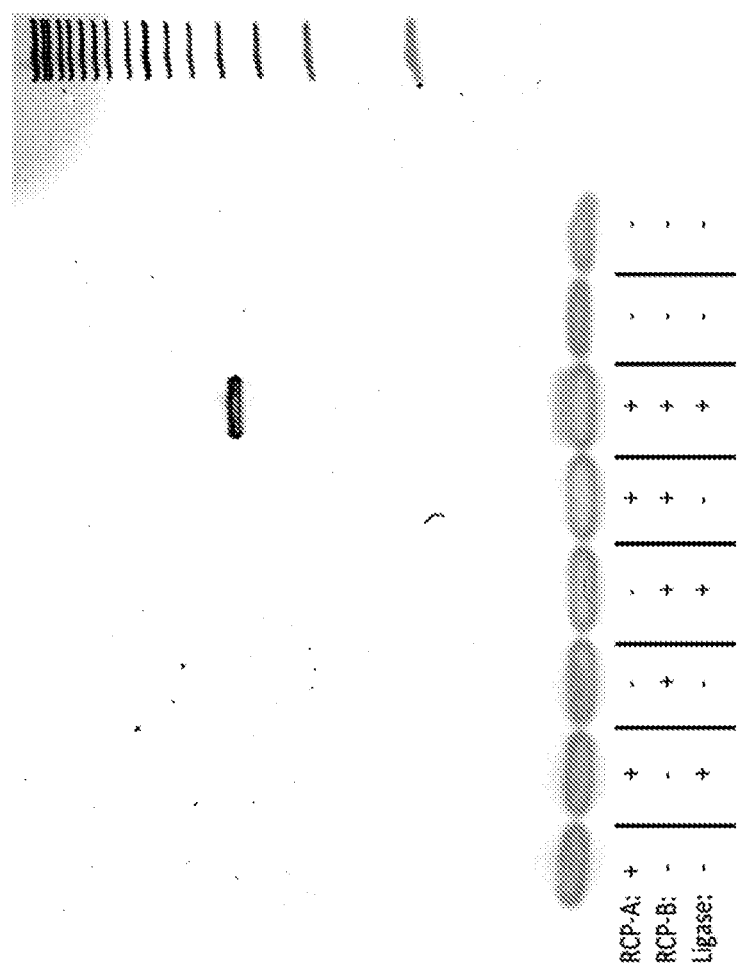
FIG. 14 is a gel showing that the formation of PCR products is dependent on the presence of ligase and both RCP types.

Validation of PCR product specificity: A control experiment was performed to confirm that the PCR product formed after ligation was dependent on the presence of the ligase enzyme and the presence of both nicked RCA products. Samples where either one or several components were not added to the reaction were PCR amplified and run on a TBE PAGE gel (FIG. 14). The results confirmed that PCR product formation was dependent on ligase and both nicked RCP types being present.

Sequencing results: A series of data filtering steps were performed on the 74 million reads generated following sequencing of the PCR product. In short, the filtering steps consisted of removing reads that were shorter than the expected length, did not contain common sequence motifs expected at certain positions and reads only observed once in the data.

The combination of DNA pixel barcodes from each read describes two DNA pixels that were in proximity to each other and were used as edges to construct an undirected graph from the data.

Figure 15:
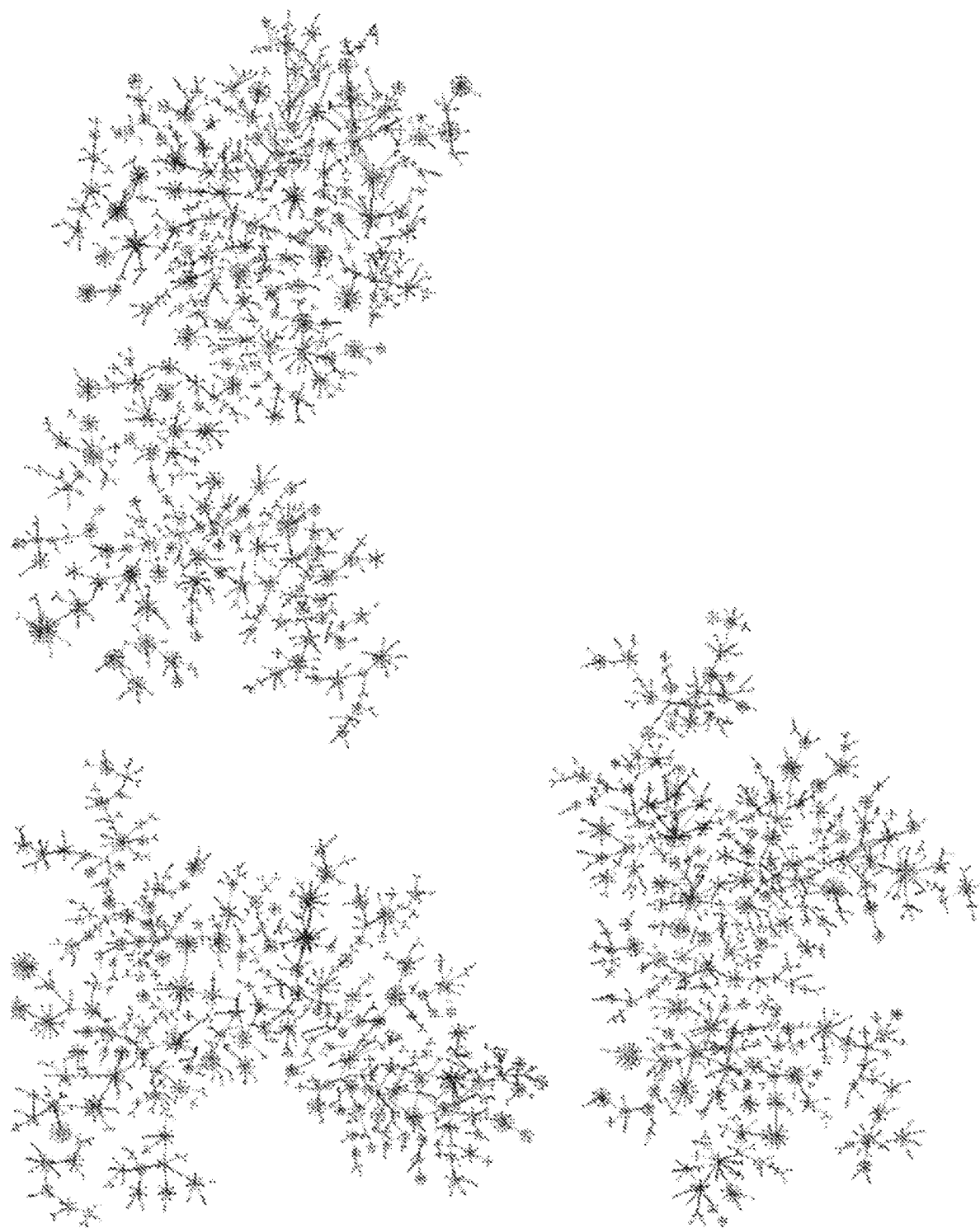
FIG. 15 is a graph showing interconnected DNA pixel barcodes. The 3 largest components of the graph are shown in this figure.

The undirected graph comprised 61 separate graph components (clusters) of at least 500 DNA pixels (nodes) in size. In addition, the graph comprised a large set of small components of size 2. FIG. 15 shows a visualization of the 3 largest components of the graph. Multiple antibodies are represented in each cluster, which are discernable by their barcodes.

What is claimed is:

1. A complex comprising multiple nucleic acid molecules that are hybridized together, each comprising, from 5' to 3':
   i. a first complementary sequence;
   ii. a spacer sequence; and
   iii. a second complementary sequence;
   wherein the molecules further comprise:
   iv. a 5' end sequence that is 5' of the first complementary sequence and terminates in
      a 5' phosphate; and/or
      a 3' end sequence that is 3' of the second complementary sequence and terminates
      in a 3' hydroxyl;
   wherein, in the complex: i. the first complementary sequence of one molecule is directly or indirectly hybridized with the second complementary sequence of another molecule in the complex and ii. the spacer sequence and the 3' and/or 5' end sequences are single-stranded, and
   wherein the complex is tethered to a cell.

2. The complex of claim 1, wherein the first and second complementary sequences are complementary to one another, and, in the complex: the first complementary sequence of one molecule is directly hybridized with the second complementary sequence of another molecule in the complex.

3. The complex of claim 1, wherein the first and second complementary sequences are complementary to a splint nucleic acid, and, in the complex: the first complementary sequence of one molecule is indirectly hybridized with the second complementary sequence of another molecule in the complex via the splint nucleic acid.

4. The complex of claim 3, wherein the splint nucleic acid is an oligonucleotide.

5. The complex of claim 1, wherein the nucleic acid molecules comprise a 3' end sequence that is 3' of the second complementary sequence and terminates in a 3' hydroxyl.

6. The complex of claim 1, wherein the nucleic acid molecules comprise a 5' end sequence that is 5' of the first complementary sequence and terminates in a 5' phosphate.

7. The complex of claim 1, wherein the complex comprises at least 100 nucleic acid molecules.

8. The complex of claim 1, wherein the first complementary sequence, the spacer sequence, the second complementary sequence, and the 3' or 5' end sequences are identical in all of the molecules.

9. The complex of claim 1, wherein the first and second complementary sequences, the spacer sequence, and the 3' or 5' end sequences are independently each at least 8 nts in length.

10. The complex of claim 1, wherein the at least one of the nucleic acid molecules of the complex is linked to a binding agent.

11. The complex of claim 10, wherein the binding agent is an antibody or oligonucleotide probe.

12. The complex of claim 1, wherein, in the complex: the first complementary sequence of one molecule is directly hybridized with the second complementary sequence of another molecule in the complex.

13. A population of complexes of claim 1.

14. The population of claim 13, wherein the nucleic acid molecules of each complex comprise a unique identifier sequence in the spacer sequence or the 3' and/or 5' end sequence, wherein the unique identifier sequence is the same in each nucleic acid molecule within a complex but different in different complexes.

15. The population of claim 13, wherein the population comprises at least 1000 of the complexes.

16. An assay method comprising:
   hybridizing a complex of claim 1 with a target polynucleotide, wherein the 3' or 5' end sequence of a nucleic acid molecule of the complex hybridizes with the target polynucleotide to produce a duplex;
   extending the nucleic acid molecule or the target polynucleotide using the other member of the duplex as a template to produce an extension product; and
   sequencing the extension product.

17. The assay method of claim 16, wherein the extending is done by ligation.

18. The assay method of claim 16, wherein the extending is done by a polymerase.

* * * * *

SEQUENCE LISTING

<160> NUMBER OF SEQ ID NOS: 48

<210> SEQ ID NO 1
<211> LENGTH: 105
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (46)..(61)
<223> OTHER INFORMATION: n is a, c, g, or t

<400> SEQUENCE: 1
ggatcgcagc ctagcgctga tgatagctgc gatcctcgac gcctgnnnnn nnnnnnnnnn    60
nagatcggaa gagcacacgt ctgaactcca gtcaccaggc gtcga                   105

<210> SEQ ID NO 2
<211> LENGTH: 100
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (40)..(55)
<223> OTHER INFORMATION: n is a, c, g, or t

<400> SEQUENCE: 2
tcgacgcctg tctttcccta cacgacgctc ttccgatctn nnnnnnnnn nnnnncaggc    60 gtcgatggca gtgcgtagcc tgggaatact cgcactgcca                        100

<210> SEQ ID NO 3
<211> LENGTH: 20
<212> TYPE: DNA
<213> ORGANISM: Artificial Sequence
<220> FEATURE:
<223> OTHER INFORMATION: synthetic sequence

<400> SEQUENCE: 3
gacgtgtgct cttccgatct                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic sequence

<400> SEQUENCE: 4
agatcggaag agcgtcgtgt                                               20

<210> SEQ ID NO 5
<211> LENGTH: 66
<212> TYPE: DNA
<213> ORGANISM: Artificial Sequence
<220> FEATURE:
<223> OTHER INFORMATION: synthetic sequence

<400> SEQUENCE: 5
caagcagaag acggcatacg agataaccgc gggtgactgg agttcagacg tgtgctcttc    60
cgatct                                                              66

<210> SEQ ID NO 6
<211> LENGTH: 58
<212> TYPE: DNA
<213> ORGANISM: Artificial Sequence
<220> FEATURE:
<223> OTHER INFORMATION: synthetic sequence

<400> SEQUENCE: 6
aatgatacgg cgaccaccga gatctacact ctttccctac acgacgctct tccgatct      58

<210> SEQ ID NO 7
<211> LENGTH: 90
<212> TYPE: DNA
<213> ORGANISM: Artificial Sequence
<220> FEATURE:

```
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 7
gtgactggag ttcagacgtg tgctcttccg atctnnnnnn nnnntccctt gcgatttacn    60
nnnnnnnngc tttaaggccg gtcctagcaa                                    90

<210> SEQ ID NO 8
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 8
gtgactggag ttcagacgtg tgctcttccg atctnnnnnn nnnntatccc ttgggatggn    60
nnnnnnnngc tttaaggccg gtcctagcaa                                    90

<210> SEQ ID NO 9
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 9
gtgactggag ttcagacgtg tgctcttccg atctnnnnnn nnnnctgggc aattactcgn    60
nnnnnnnngc tttaaggccg gtcctagcaa                                    90

<210> SEQ ID NO 10
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 10
gtgactggag ttcagacgtg tgctcttccg atctnnnnnn nnnngccgga cgacattaan    60
```
nnnnnnnngc ttaaggccg gtcctagcaa          90

<210> SEQ ID NO 11
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 11
gtgactggag ttcagacgtg tgctcttccg atctnnnnnn nnnnttctgg gtccctagan          60
nnnnnnnngc ttaaggccg gtcctagcaa          90

<210> SEQ ID NO 12
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 12
gtgactggag ttcagacgtg tgctcttccg atctnnnnnn nnnngtctct tggcttaaan          60
nnnnnnnngc ttaaggccg gtcctagcaa          90

<210> SEQ ID NO 13
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 13
gtgactggag ttcagacgtg tgctcttccg atctnnnnnn nnnnaatagc gagcaagtan          60
nnnnnnnngc ttaaggccg gtcctagcaa          90

<210> SEQ ID NO 14
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)

```
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 14
gtgactggag ttcagacgtg tgctcttccg atctnnnnnn nnnngctgcg ctttccattn      60
nnnnnnnngc tttaaggccg gtcctagcaa                                      90

<210> SEQ ID NO 15
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 15
gtgactggag ttcagacgtg tgctcttccg atctnnnnnn nnnncaatca gacctatgan      60
nnnnnnnngc tttaaggccg gtcctagcaa                                      90

<210> SEQ ID NO 16
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 16
gtgactggag ttcagacgtg tgctcttccg atctnnnnnn nnnnatatgt atcacgcgan      60
nnnnnnnngc tttaaggccg gtcctagcaa                                      90

<210> SEQ ID NO 17
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 17
gtgactggag ttcagacgtg tgctcttccg atctnnnnnn nnnntcaatc cttccgcttn      60
nnnnnnnngc tttaaggccg gtcctagcaa                                      90
```

```
<210> SEQ ID NO 18
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 18
gtgactggag ttcagacgtg tgctcttccg atctnnnnnn nnnnctccga atcatgttgn      60
nnnnnnnngc tttaaggccg gtcctagcaa                                      90

<210> SEQ ID NO 19
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 19
gtgactggag ttcagacgtg tgctcttccg atctnnnnnn nnnngtccct gcaacttgan      60
nnnnnnnngc tttaaggccg gtcctagcaa                                      90

<210> SEQ ID NO 20
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 20
gtgactggag ttcagacgtg tgctcttccg atctnnnnnn nnnntcccac ttccgctttn      60
nnnnnnnngc tttaaggccg gtcctagcaa                                      90

<210> SEQ ID NO 21
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
```

<223> OTHER INFORMATION: n is a, c, g, or t

<400> SEQUENCE: 21
gtgactggag ttcagacgtg tgctcttccg atctnnnnnn nnnntggatt cccggacttn    60
nnnnnnnngc tttaaggccg gtcctagcaa                                    90

<210> SEQ ID NO 22
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 22
gtgactggag ttcagacgtg tgctcttccg atctnnnnnn nnnncgcgaa cataagaagn    60
nnnnnnnngc tttaaggccg gtcctagcaa                                    90

<210> SEQ ID NO 23
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 23
gtgactggag ttcagacgtg tgctcttccg atctnnnnnn nnnncagtcg tggtagatan    60
nnnnnnnngc tttaaggccg gtcctagcaa                                    90

<210> SEQ ID NO 24
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 24
gtgactggag ttcagacgtg tgctcttccg atctnnnnnn nnnnatatgt cagagcaccn    60
nnnnnnnngc tttaaggccg gtcctagcaa                                    90

<210> SEQ ID NO 25
<211> LENGTH: 90
<212> TYPE: DNA
<213> ORGANISM: Artificial Sequence

```
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 25
gtgactggag ttcagacgtg tgctcttccg atctnnnnnn nnnnggtggc tagataatgn    60
nnnnnnnngc tttaaggccg gtcctagcaa                                     90

<210> SEQ ID NO 26
<211> LENGTH: 90
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (35)..(44)
<223> OTHER INFORMATION: n is a, c, g, or t
<220> FEATURE:
<221> NAME/KEY: misc_feature
<222> LOCATION: (60)..(68)
<223> OTHER INFORMATION: n is a, c, g, or t

<400> SEQUENCE: 26
gtgactggag ttcagacgtg tgctcttccg atctnnnnnn nnnngagatg tctgcaactn    60
nnnnnnnngc tttaaggccg gtcctagcaa                                     90

<210> SEQ ID NO 27
<211> LENGTH: 57
<212> TYPE: DNA
<213> ORGANISM: Artificial Sequence
<220> FEATURE:
<223> OTHER INFORMATION: synthetic sequence

<400> SEQUENCE: 27
cctagcgctg atgatagttt gtaaatcgca agggatttcg tagcctggga atactcg       57

<210> SEQ ID NO 28
<211> LENGTH: 57
<212> TYPE: DNA
<213> ORGANISM: Artificial Sequence
<220> FEATURE:
<223> OTHER INFORMATION: synthetic sequence

<400> SEQUENCE: 28
cctagcgctg atgatagttt gtaaatcgca agggatttcg tagcctggga atactcg       57

<210> SEQ ID NO 29
<211> LENGTH: 57
<212> TYPE: DNA
<213> ORGANISM: Artificial Sequence
<220> FEATURE:
<223> OTHER INFORMATION: synthetic sequence

<400> SEQUENCE: 29
cctagcgctg atgatagttt ccatcccaag ggatatttcg tagcctggga atactcg       57

<210> SEQ ID NO 30
<211> LENGTH: 57
<212> TYPE: DNA
```

<213> ORGANISM: Artificial Sequence
<220> FEATURE:
<223> OTHER INFORMATION: synthetic sequence

<400> SEQUENCE: 30
cctagcgctg atgatagttt cgagtaattg cccagtttcg tagcctggga atactcg    57

<210> SEQ ID NO 31
<211> LENGTH: 57
<212> TYPE: DNA
<213> ORGANISM: Artificial Sequence
<220> FEATURE:
<223> OTHER INFORMATION: synthetic sequence

<400> SEQUENCE: 31
cctagcgctg atgatagttt ttaatgtcgt ccggctttcg tagcctggga atactcg    57

<210> SEQ ID NO 32
<211> LENGTH: 57
<212> TYPE: DNA
<213> ORGANISM: Artificial Sequence
<220> FEATURE:
<223> OTHER INFORMATION: synthetic sequence

<400> SEQUENCE: 32
cctagcgctg atgatagttt tctagggacc cagaatttcg tagcctggga atactcg    57

<210> SEQ ID NO 33
<211> LENGTH: 57
<212> TYPE: DNA
<213> ORGANISM: Artificial Sequence
<220> FEATURE:
<223> OTHER INFORMATION: synthetic sequence

<400> SEQUENCE: 33
cctagcgctg atgatagttt tttaagccaa gagactttcg tagcctggga atactcg    57

<210> SEQ ID NO 34
<211> LENGTH: 57
<212> TYPE: DNA
<213> ORGANISM: Artificial Sequence
<220> FEATURE:
<223> OTHER INFORMATION: synthetic sequence

<400> SEQUENCE: 34
cctagcgctg atgatagttt tacttgctcg ctattttcg tagcctggga atactcg    57

<210> SEQ ID NO 35
<211> LENGTH: 57
<212> TYPE: DNA
<213> ORGANISM: Artificial Sequence
<220> FEATURE:
<223> OTHER INFORMATION: synthetic sequence

<400> SEQUENCE: 35
cctagcgctg atgatagttt aatggaaagc gcagctttcg tagcctggga atactcg    57

<210> SEQ ID NO 36
<211> LENGTH: 57
<212> TYPE: DNA
<213> ORGANISM: Artificial Sequence
<220> FEATURE:
<223> OTHER INFORMATION: synthetic sequence

<400> SEQUENCE: 36
cctagcgctg atgatagttt tcataggtct gattgtttcg tagcctggga atactcg    57

<210> SEQ ID NO 37
<211> LENGTH: 57
<212> TYPE: DNA
<213> ORGANISM: Artificial Sequence
<220> FEATURE:
<223> OTHER INFORMATION: synthetic sequence

<400> SEQUENCE: 37
cctagcgctg atgatagttt tcgcgtgata catattttcg tagcctggga atactcg       57

<210> SEQ ID NO 38
<211> LENGTH: 57
<212> TYPE: DNA
<213> ORGANISM: Artificial Sequence
<220> FEATURE:
<223> OTHER INFORMATION: synthetic sequence

<400> SEQUENCE: 38
cctagcgctg atgatagttt aagcggaagg attgatttcg tagcctggga atactcg       57

<210> SEQ ID NO 39
<211> LENGTH: 57
<212> TYPE: DNA
<213> ORGANISM: Artificial Sequence
<220> FEATURE:
<223> OTHER INFORMATION: synthetic sequence

<400> SEQUENCE: 39
cctagcgctg atgatagttt caacatgatt cggagtttcg tagcctggga atactcg       57

<210> SEQ ID NO 40
<211> LENGTH: 57
<212> TYPE: DNA
<213> ORGANISM: Artificial Sequence
<220> FEATURE:
<223> OTHER INFORMATION: synthetic sequence

<400> SEQUENCE: 40
cctagcgctg atgatagttt tcaagttgca gggactttcg tagcctggga atactcg       57

<210> SEQ ID NO 41
<211> LENGTH: 57
<212> TYPE: DNA
<213> ORGANISM: Artificial Sequence
<220> FEATURE:
<223> OTHER INFORMATION: synthetic sequence

<400> SEQUENCE: 41
cctagcgctg atgatagttt aaagcggaag tgggatttcg tagcctggga atactcg       57

<210> SEQ ID NO 42
<211> LENGTH: 57
<212> TYPE: DNA
<213> ORGANISM: Artificial Sequence
<220> FEATURE:
<223> OTHER INFORMATION: synthetic sequence

<400> SEQUENCE: 42
cctagcgctg atgatagttt aagtccggga atccatttcg tagcctggga atactcg       57

<210> SEQ ID NO 43
<211> LENGTH: 57
<212> TYPE: DNA
<213> ORGANISM: Artificial Sequence
<220> FEATURE:

<223> OTHER INFORMATION: synthetic sequence

<400> SEQUENCE: 43
cctagcgctg atgatagttt cttcttatgt tcgcgtttcg tagcctggga atactcg    57

<210> SEQ ID NO 44
<211> LENGTH: 57
<212> TYPE: DNA
<213> ORGANISM: Artificial Sequence
<220> FEATURE:
<223> OTHER INFORMATION: synthetic sequence

<400> SEQUENCE: 44
cctagcgctg atgatagttt tatctaccac gactgtttcg tagcctggga atactcg    57

<210> SEQ ID NO 45
<211> LENGTH: 57
<212> TYPE: DNA
<213> ORGANISM: Artificial Sequence
<220> FEATURE:
<223> OTHER INFORMATION: synthetic sequence

<400> SEQUENCE: 45
cctagcgctg atgatagttt ggtgctctga catattttcg tagcctggga atactcg    57

<210> SEQ ID NO 46
<211> LENGTH: 57
<212> TYPE: DNA
<213> ORGANISM: Artificial Sequence
<220> FEATURE:
<223> OTHER INFORMATION: synthetic sequence

<400> SEQUENCE: 46
cctagcgctg atgatagttt cattatctag ccacctttcg tagcctggga atactcg    57

<210> SEQ ID NO 47
<211> LENGTH: 10
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (6)..(10)
<223> OTHER INFORMATION: n is a, c, g, or t

<400> SEQUENCE: 47 ggatcnnnnn    10

<210> SEQ ID NO 48
<211> LENGTH: 10
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (6)..(10)
<223> OTHER INFORMATION: n is a, c, g, or t

<400> SEQUENCE: 48 cctagnnnnn    10